(12) United States Patent
Woloszko et al.

(10) Patent No.: US 7,988,689 B2
(45) Date of Patent: *Aug. 2, 2011

(54) ELECTROSURGICAL APPARATUS AND METHODS FOR TREATMENT AND REMOVAL OF TISSUE

(75) Inventors: Jean Woloszko, Austin, TX (US); Robert H. Dahla, Mountain View, CA (US)

(73) Assignee: ArthroCare Corporation, Austin, TX (US)

( * ) Notice: Subject to any disclaimer, the term of this patent is extended or adjusted under 35 U.S.C. 154(b) by 988 days.

This patent is subject to a terminal disclaimer.

(21) Appl. No.: 11/856,646

(22) Filed: Sep. 17, 2007

(65) Prior Publication Data

US 2008/0004621 A1 Jan. 3, 2008

Related U.S. Application Data

(60) Continuation of application No. 10/068,533, filed on Feb. 5, 2002, now Pat. No. 7,270,661, which is a continuation-in-part of application No. 09/586,295, filed on Jun. 2, 2000, now Pat. No. 7,678,069, which is a division of application No. 09/248,763, filed on Feb. 12, 1999, now Pat. No. 6,149,620.

(60) Provisional application No. 60/299,094, filed on Jun. 18, 2001, provisional application No. 60/096,150, filed on Aug. 11, 1998, provisional application No. 60/098,122, filed on Aug. 27, 1998.

(51) Int. Cl.
*A61B 18/14* (2006.01)
(52) U.S. Cl. ............................................. 606/41; 606/48
(58) Field of Classification Search .................... 606/41, 606/42, 45–50
See application file for complete search history.

(56) References Cited

U.S. PATENT DOCUMENTS

| 2,050,904 A | 4/1936 | Trice ................................ 219/31 |
| 2,056,377 A | 10/1939 | Wappler ......................... 125/303 |
| 3,633,425 A | 1/1972 | Sanford ........................... 73/356 |

(Continued)

FOREIGN PATENT DOCUMENTS

DE 3119735 1/1983

(Continued)

OTHER PUBLICATIONS

Buchelt, et al. "Excimer Laser Ablation of Fibrocartilage: An In Vitro and In Vivo Study", Lasers in Surgery and Medicine, vol. 11, pp. 271-279, 1991.

(Continued)

*Primary Examiner* — Michael Peffley
(74) *Attorney, Agent, or Firm* — Matthew Scheele; Brian Szymczak

(57) ABSTRACT

Apparatus and methods for ablating, severing, cutting, shrinking, coagulating, or otherwise modifying a target tissue to be treated. In a method for treating a target tissue, an active electrode of an electrosurgical probe is positioned in at least close proximity to the target tissue in the presence of an electrically conductive fluid. A high frequency voltage is then applied between the active electrode and a return electrode, wherein, the high frequency voltage is sufficient to volumetrically remove (ablate), sever, or modify at least a portion of the target tissue. The probe comprises a multi-lumen shaft having a plurality of internal lumens, and a return electrode coil oriented substantially parallel to the shaft distal end. The active electrode may be in the form of a metal disc, a hook, or an active electrode coil. In the latter embodiment, the active electrode coil is typically arranged substantially orthogonal to the return electrode coil. Methods of making an active electrode coil, a return electrode coil, and an electrosurgical probe are also disclosed.

16 Claims, 28 Drawing Sheets

U.S. PATENT DOCUMENTS

| | | | |
|---|---|---|---|
| 3,707,149 A | 12/1972 | Hao et al. | 128/303.14 |
| 3,718,617 A | 2/1973 | Royal | 260/30.4 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,963,030 A | 6/1976 | Newton | 606/40 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,114,623 A | 9/1978 | Meinke et al. | 606/39 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,301,801 A | 11/1981 | Schneiderman | 606/38 |
| 4,326,529 A | 4/1982 | Doss et al. | 128/303 |
| 4,346,715 A | 8/1982 | Gammell | 607/99 |
| 4,363,324 A | 12/1982 | Kusserow | 607/64 |
| 4,378,801 A | 4/1983 | Oosten | 606/37 |
| 4,381,007 A | 4/1983 | Doss | 128/303 |
| 4,418,692 A | 12/1983 | Guay | 606/42 |
| 4,474,179 A | 10/1984 | Koch | 606/40 |
| 4,476,862 A | 10/1984 | Pao | 128/303 |
| 4,509,532 A | 4/1985 | DeVries | 128/736 |
| 4,520,818 A | 6/1985 | Mickiewicz | 606/40 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,750,902 A | 6/1988 | Wuchinich et al. | 604/22 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,860,752 A | 8/1989 | Turner | 607/102 |
| 4,898,169 A | 2/1990 | Norman et al. | 606/42 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/40 |
| 5,026,387 A | 6/1991 | Thomas | 606/169 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,098,431 A | 3/1992 | Rydell | 606/48 |
| 5,099,840 A | 3/1992 | Goble et al. | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,174,304 A | 12/1992 | Latina et al. | 607/141 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,336,443 A | 8/1994 | Odashima | 252/511 |
| 5,342,357 A | 8/1994 | Nardella | 606/40 |
| 5,348,554 A | 9/1994 | Imran et al. | 606/41 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |

| | | | |
|---|---|---|---|
| 5,458,597 A | 10/1995 | Edwards et al. ............... 606/41 |
| 5,472,443 A | 12/1995 | Cordis et al. ............... 606/48 |
| 5,486,161 A | 1/1996 | Lax et al. ............... 604/22 |
| 5,496,312 A | 3/1996 | Klicek ............... 606/34 |
| 5,496,314 A | 3/1996 | Eggers ............... 606/41 |
| 5,496,317 A | 3/1996 | Goble et al. ............... 606/48 |
| 5,505,730 A | 4/1996 | Edwards et al. ............... 606/41 |
| 5,507,743 A | 4/1996 | Edwards et al. ............... 313/639 |
| 5,514,130 A | 5/1996 | Baker ............... 606/41 |
| 5,540,683 A | 7/1996 | Ichikawa et al. ............... 606/40 |
| 5,542,915 A | 8/1996 | Edwards et al. ............... 604/22 |
| 5,549,598 A | 8/1996 | O'Donnell, Jr. ............... 606/6 |
| 5,554,152 A | 9/1996 | Aita ............... 606/7 |
| 5,556,397 A | 9/1996 | Long et al. ............... 606/48 |
| 5,562,703 A | 10/1996 | Desai ............... 606/210 |
| 5,569,242 A | 10/1996 | Lax et al. ............... 606/42 |
| 5,571,100 A | 11/1996 | Goble et al. ............... 606/41 |
| 5,573,533 A | 11/1996 | Strul ............... 606/34 |
| 5,584,872 A | 12/1996 | LaFontaine et al. ............... 607/117 |
| 5,588,960 A | 12/1996 | Edwards et al. ............... 604/20 |
| 5,599,350 A | 2/1997 | Schulze et al. ............... 606/51 |
| 5,609,151 A | 3/1997 | Mulier et al. ............... 128/642 |
| 5,633,578 A | 5/1997 | Eggers et al. ............... 323/301 |
| 5,634,921 A | 6/1997 | Hood et al. ............... 606/5 |
| 5,643,304 A | 7/1997 | Schechter et al. ............... 606/171 |
| 5,647,869 A | 7/1997 | Goble et al. ............... 606/37 |
| 5,658,278 A | 8/1997 | Imran et al. ............... 606/41 |
| 5,660,567 A | 8/1997 | Nierlich et al. ............... 439/620.21 |
| 5,662,680 A | 9/1997 | Desai ............... 606/210 |
| 5,676,693 A | 10/1997 | LaFontaine et al. ............... 607/116 |
| 5,681,282 A | 10/1997 | Eggers et al. ............... 604/114 |
| 5,683,366 A | 11/1997 | Eggers et al. ............... 604/114 |
| 5,697,281 A | 12/1997 | Eggers et al. ............... 604/114 |
| 5,697,536 A | 12/1997 | Eggers et al. ............... 604/114 |
| 5,697,882 A | 12/1997 | Eggers et al. ............... 604/114 |
| 5,697,909 A | 12/1997 | Eggers et al. ............... 604/114 |
| 5,697,927 A | 12/1997 | Imran et al. ............... 606/41 |
| 5,700,262 A | 12/1997 | Acosta et al. ............... 606/48 |
| 5,715,817 A | 2/1998 | Stevens-Wright et al. ............... 600/373 |
| 5,722,975 A | 3/1998 | Edwards et al. ............... 606/41 |
| 5,725,524 A | 3/1998 | Mulier et al. ............... 606/41 |
| 5,749,869 A | 5/1998 | Lindenmeier et al. ............... 606/34 |
| 5,749,871 A | 5/1998 | Hood et al. ............... 606/50 |
| 5,749,914 A | 5/1998 | Janssen ............... 607/116 |
| 5,755,753 A | 5/1998 | Knowlton ............... 607/98 |
| 5,766,153 A | 6/1998 | Eggers et al. ............... 604/114 |
| 5,769,847 A | 6/1998 | Panescu et al. ............... 606/42 |
| 5,785,705 A | 7/1998 | Baker ............... 606/41 |
| 5,786,578 A | 7/1998 | Christy et al. ............... 219/720 |
| 5,800,429 A | 9/1998 | Edwards ............... 606/41 |
| 5,807,395 A | 9/1998 | Mulier et al. ............... 606/41 |
| 5,810,764 A | 9/1998 | Eggers et al. ............... 604/23 |
| 5,810,802 A | 9/1998 | Panescu et al. ............... 606/31 |
| 5,810,809 A | 9/1998 | Rydell ............... 606/49 |
| 5,836,875 A | 11/1998 | Webster, Jr. ............... 600/374 |
| 5,843,019 A | 12/1998 | Eggers et al. ............... 604/22 |
| 5,860,951 A | 1/1999 | Eggers ............... 604/510 |
| 5,860,974 A | 1/1999 | Abele ............... 606/41 |
| 5,860,975 A | 1/1999 | Goble et al. ............... 606/45 |
| 5,871,469 A | 2/1999 | Eggers et al. ............... 604/114 |
| 5,873,855 A | 2/1999 | Eggers et al. ............... 604/114 |
| 5,873,877 A | 2/1999 | McGaffigan ............... 606/41 |
| 5,885,277 A | 3/1999 | Korth ............... 606/35 |
| 5,888,198 A | 3/1999 | Eggers et al. ............... 604/114 |
| 5,891,095 A | 4/1999 | Eggers et al. ............... 604/114 |
| 5,891,134 A | 4/1999 | Goble et al. ............... 606/27 |
| 5,897,553 A | 4/1999 | Mulier ............... 606/41 |
| 5,902,272 A | 5/1999 | Eggers et al. ............... 604/114 |
| 5,944,715 A | 8/1999 | Goble et al. ............... 606/41 |
| 5,954,716 A | 9/1999 | Sharkey et al. ............... 606/32 |
| 5,964,786 A | 10/1999 | Ochs et al. ............... 607/5 |
| 6,004,319 A | 12/1999 | Goble et al. ............... 606/48 |
| 6,013,076 A | 1/2000 | Goble et al. ............... 606/41 |
| 6,015,406 A | 1/2000 | Goble et al. ............... 606/41 |
| 6,024,733 A | 2/2000 | Eggers et al. ............... 604/500 |
| 6,027,501 A | 2/2000 | Goble et al. ............... 606/41 |
| 6,039,734 A | 3/2000 | Goble et al. ............... 606/41 |
| 6,047,700 A | 4/2000 | Eggers et al. ............... 128/898 |
| 6,056,746 A | 5/2000 | Goble et al. ............... 606/48 |
| 6,063,079 A | 5/2000 | Hovda et al. ............... 606/41 |
| 6,066,134 A | 5/2000 | Eggers et al. ............... 606/32 |
| 6,068,628 A | 5/2000 | Fanton et al. ............... 606/41 |
| 6,074,386 A | 6/2000 | Goble et al. ............... 606/34 |
| 6,090,106 A | 7/2000 | Goble et al. ............... 606/41 |
| 6,093,186 A | 7/2000 | Goble ............... 606/34 |
| 6,102,046 A | 8/2000 | Weinstein et al. ............... 128/898 |
| 6,105,581 A | 8/2000 | Eggers et al. ............... 128/898 |
| 6,109,268 A | 8/2000 | Thapliyal et al. ............... 128/898 |
| 6,117,109 A | 9/2000 | Eggers et al. ............... 604/114 |
| 6,126,682 A | 10/2000 | Sharkey et al. ............... 607/96 |
| 6,142,992 A | 11/2000 | Cheng et al. ............... 606/34 |
| 6,149,620 A | 11/2000 | Baker et al. ............... 604/22 |
| 6,159,194 A | 12/2000 | Eggers et al. ............... 604/500 |
| 6,159,208 A | 12/2000 | Hovda et al. ............... 606/41 |
| 6,162,217 A | 12/2000 | Kannenberg et al. ............... 606/34 |
| 6,168,593 B1 | 1/2001 | Sharkey et al. ............... 606/34 |
| 6,174,309 B1 | 1/2001 | Wrublewski et al. ............... 606/45 |
| 6,179,824 B1 | 1/2001 | Eggers et al. ............... 604/500 |
| 6,179,836 B1 | 1/2001 | Eggers et al. ............... 606/45 |
| 6,183,469 B1 | 2/2001 | Thapliyal et al. ............... 606/41 |
| 6,190,381 B1 | 2/2001 | Olsen et al. ............... 606/32 |
| 6,197,021 B1 | 3/2001 | Panescu et al. ............... 606/31 |
| 6,203,542 B1 | 3/2001 | Ellsberry et al. ............... 606/41 |
| 6,210,402 B1 | 4/2001 | Olsen et al. ............... 606/32 |
| 6,210,405 B1 | 4/2001 | Goble et al. ............... 606/41 |
| 6,224,592 B1 | 5/2001 | Eggers et al. ............... 606/32 |
| 6,228,078 B1 | 5/2001 | Eggers ............... 606/32 |
| 6,228,081 B1 | 5/2001 | Goble ............... 606/34 |
| 6,234,178 B1 | 5/2001 | Goble ............... 606/32 |
| 6,235,020 B1 | 5/2001 | Cheng et al. ............... 606/34 |
| 6,237,604 B1 | 5/2001 | Burnside et al. ............... 128/897 |
| 6,238,391 B1 | 5/2001 | Olsen et al. ............... 606/41 |
| 6,238,393 B1 | 5/2001 | Mulier et al. ............... 606/41 |
| 6,254,600 B1 | 7/2001 | Willink et al. ............... 606/41 |
| 6,261,286 B1 | 7/2001 | Goble et al. ............... 606/34 |
| 6,261,311 B1 | 7/2001 | Sharkey et al. ............... 607/96 |
| 6,264,652 B1 | 7/2001 | Eggers et al. ............... 606/41 |
| 6,270,460 B1 | 8/2001 | McCartan et al. ............... 600/459 |
| 6,277,112 B1 | 8/2001 | Underwood et al. ............... 606/32 |
| 6,280,441 B1 | 8/2001 | Ryan ............... 606/45 |
| 6,283,961 B1 | 9/2001 | Underwood et al. ............... 604/41 |
| 6,293,942 B1 | 9/2001 | Goble et al. ............... 606/38 |
| 6,296,636 B1 | 10/2001 | Cheng et al. ............... 606/32 |
| 6,296,638 B1 | 10/2001 | Davison et al. ............... 606/41 |
| 6,306,134 B1 | 10/2001 | Goble et al. ............... 606/42 |
| 6,308,089 B1 | 10/2001 | von der Rur et al. ............... 600/338 |
| 6,309,387 B1 | 10/2001 | Eggers et al. ............... 606/41 |
| 6,312,408 B1 | 11/2001 | Eggers et al. ............... 604/114 |
| 6,322,549 B1 | 11/2001 | Eggers et al. ............... 604/500 |
| 6,346,104 B2 | 2/2002 | Daly et al. ............... 606/34 |
| 6,346,107 B1 | 2/2002 | Cucin ............... 606/49 |
| 6,355,032 B1 | 3/2002 | Hovda et al. ............... 606/32 |
| 6,363,937 B1 | 4/2002 | Hovda et al. ............... 128/898 |
| 6,364,877 B1 | 4/2002 | Goble et al. ............... 606/34 |
| 6,379,351 B1 | 4/2002 | Thapliyal et al. ............... 606/41 |
| 6,391,025 B1 | 5/2002 | Weinstein et al. ............... 606/41 |
| 6,409,722 B1 | 6/2002 | Hoey et al. ............... 606/34 |
| 6,416,507 B1 | 7/2002 | Eggers et al. ............... 606/32 |
| 6,416,508 B1 | 7/2002 | Eggers et al. ............... 606/32 |
| 6,416,509 B1 | 7/2002 | Goble et al. ............... 606/37 |
| 6,432,103 B1 | 8/2002 | Ellsberry et al. ............... 606/41 |
| 6,440,129 B1 | 8/2002 | Simpson ............... 606/42 |
| 6,468,274 B1 | 10/2002 | Alleyne et al. ............... 606/32 |
| 6,468,275 B1 | 10/2002 | Wampler et al. ............... 606/48 |
| 6,482,201 B1 | 11/2002 | Olsen et al. ............... 606/41 |
| 6,514,250 B1 | 2/2003 | Jahns et al. ............... 606/41 |
| 6,517,498 B1 | 2/2003 | Burbank et al. ............... 600/564 |
| 6,530,922 B2 | 3/2003 | Cosman ............... 606/34 |
| 6,558,382 B2 | 5/2003 | Jahns et al. ............... 606/41 |
| 6,565,560 B1 | 5/2003 | Goble et al. ............... 606/41 |
| 6,578,579 B2 | 6/2003 | Burnside ............... 128/897 |
| 6,589,237 B2 | 7/2003 | Woloszko et al. ............... 606/41 |
| 6,602,248 B1 | 8/2003 | Sharps et al. ............... 606/32 |
| 6,620,156 B1 | 9/2003 | Garito et al. ............... 606/50 |
| 6,632,193 B1 | 10/2003 | Davison et al. ............... 604/22 |
| 6,632,220 B1 | 10/2003 | Eggers et al. ............... 606/41 |
| 6,635,034 B1 | 10/2003 | Cosmescu ............... 604/289 |
| 6,656,177 B2 | 12/2003 | Truckai et al. ............... 606/51 |

| | | | |
|---|---|---|---|
| 6,730,080 B2 | 5/2004 | Harano et al. | 606/38 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,866,671 B2 | 3/2005 | Tierney et al. | 606/130 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 451/6 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Ricart et al. | 606/32 |
| 7,270,661 B2 | 9/2007 | Dahla et al. | 606/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Woloszko et al. | 606/41 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,678,069 B1 | 3/2010 | Baker et al. | 604/22 |
| 7,691,101 B2 | 4/2010 | Davison et al. | 606/41 |
| 7,862,560 B2 | 1/2011 | Marion | 606/34 |
| 2001/0025177 A1 | 9/2001 | Woloszko et al. | 606/46 |
| 2002/0029036 A1 | 3/2002 | Goble et al. | 606/38 |
| 2002/0042612 A1 | 4/2002 | Hood et al. | 606/50 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208194 A1 | 11/2003 | Hovda et al. | 606/41 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2004/0024399 A1 | 2/2004 | Sharps et al. | 606/32 |
| 2004/0030330 A1 | 2/2004 | Brassell et al. | 606/41 |
| 2004/0049180 A1 | 3/2004 | Sharps et al. | 606/32 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Ricart et al. | 606/41 |
| 2005/0010205 A1 | 1/2005 | Hovda et al. | 606/32 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0273091 A1 | 12/2005 | Booth et al. | 607/99 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Hovda et al. | 606/32 |
| 2007/0282323 A1 | 12/2007 | Woloszko et al. | 606/41 |
| 2008/0077128 A1 | 3/2008 | Woloszko et al. | 606/41 |
| 2008/0154255 A1 | 6/2008 | Panos et al. | 606/33 |
| 2008/0167645 A1 | 7/2008 | Woloszko | 606/40 |
| 2008/0243116 A1 | 10/2008 | Anderson | 606/41 |
| 2008/0300590 A1 | 12/2008 | Horne et al. | 606/35 |
| 2009/0209956 A1 | 8/2009 | Marion | 606/34 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2010/0324549 A1 | 12/2010 | Marion | 606/37 |

FOREIGN PATENT DOCUMENTS

| | | |
|---|---|---|
| DE | 3930451 A1 | 3/1991 |
| EP | 423757 | 3/1996 |
| EP | 0703461 A2 | 3/1996 |
| EP | 0740926 A2 | 11/1996 |
| EP | 0 754 437 | 1/1997 |
| EP | 0 694 290 | 11/2000 |
| EP | 1334699 | 8/2003 |
| EP | 1428480 | 6/2004 |
| EP | 1707147 | 10/2006 |
| FR | 2313949 | 1/1977 |
| GB | 467502 | 6/1937 |
| GB | 2160102 | 12/1985 |
| GB | 2299216 | 9/1996 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| GB | 2333455 | 7/1999 |
| GB | 2406793 | 4/2005 |
| JP | 57-57802 | 4/1982 |
| JP | 57-117843 | 7/1982 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 94/10921 | 5/1994 |
| WO | 94/26228 | 11/1994 |
| WO | 95/34259 | 12/1995 |
| WO | 96/00040 | 1/1996 |
| WO | 96/00042 | 1/1996 |
| WO | 96/39086 | 12/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/43971 | 11/1997 |

| WO | 97/48345 | 12/1997 |
| WO | 97/48346 | 12/1997 |
| WO | 98/07468 | 2/1998 |
| WO | 98/26724 | 6/1998 |
| WO | 98/27879 | 7/1998 |
| WO | 98/27880 | 7/1998 |
| WO | 99/20213 | 4/1999 |
| WO | 99/51155 | 10/1999 |
| WO | 99/51158 | 10/1999 |
| WO | 99/56648 | 11/1999 |
| WO | 00/00098 | 1/2000 |
| WO | 00/09053 | 2/2000 |
| WO | 01/24720 | 4/2001 |
| WO | 01/87154 | 5/2001 |
| WO | 02/36028 | 5/2002 |
| WO | 02/102255 | 12/2002 |
| WO | 03/024305 | 3/2003 |
| WO | 03/092477 | 11/2003 |
| WO | 2004/026150 | 4/2004 |
| WO | 2004/071278 | 8/2004 |
| WO | 2005/125287 | 12/2005 |
| WO | 2007/006000 | 1/2007 |
| WO | 2007/056729 | 5/2007 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
PCT International Search Report for PCT/US99/14685, 1 pg, Mailed Oct. 21, 1999.
PCT Notification of International Preliminary Examination Report for PCT/US99/14685, 4 pgs, Mailed Feb. 20, 2001.
PCT International Search Report for PCT/US98/22323, 1 pg, Mailed Mar. 3, 1999.
PCT Notification of International Preliminary Examination Report for PCT/US98/22323, 5 pgs, Mailed Nov. 28, 2000.
European Search Report for EP 98953859, 2 pgs, Jul. 2, 2001.
Supplementary European Search Report for EP 98953859, 3 pgs, Oct. 18, 2001.
PCT International Search Report for PCT/US99/18289, 1 pg, Dec. 7, 1999.
PCT Notification of International Preliminary Examination Report for PCT/US99/18289, 4 pgs, Jul. 7, 2000.
European Search Report for EP 99945039.8, 3 pgs, Oct. 1, 2001.
PCT International Search Report for PCT/US02/19261, 1 pg, Mailed Sep. 18, 2002.
PCT International Preliminary Examination Report for PCT/US02/19261, 3 pgs, Mar. 25, 2003.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT Written Opinion of the International Searching Authority for PCT/US04/03614, 4 pgs, Mailed Sep. 14, 2004.
EP Communication, European Examination Report for EP 98953859.0, 3 pgs, Jun. 14, 2004.
EP Communication, European Examination Report for EP 99945039 8, 5 pgs, May 10, 2004.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
Barry et al., "The Effect of Radiofrequency-generated Thermal Energy on the Mechanical and Histologic Characteristics of the Arterial Wall in Vivo: Implications of Radiofrequency Angioplasty" American Heart Journal vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65, 1975.
Kramolowsky et al. "The Urological App of Electorsurgery" J. of Urology vol. 146, pp. 669-674, 1991.
Kramolowsky et al. "Use of 5F Bipolar Electrosurgical Probe in Endoscopic Urological Procedures" J. of Urology vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malls dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," Am J. Cardiol vol. 60, pp. 1117-1122, Nov. 1, 1987.
Malis, L., "Electrosurgery, Technical Note," J. Neursurg., vol. 85, pp. 970-975, Nov. 1996.
Malis, L., "Excerpted from a seminar by Leonard I. Malls, M.D. at the 1995 American Association of Neurological Surgeons Meeting," 1pg, 1995.
Malis, L., "Instrumentation for Microvascular Neurosurgery" Cerebrovascular Surgery, vol. 1, pp. 245-260, 1985.
Malls, L., "New Trends in Microsurgery and Applied Technology," Advanced Technology in Neurosurgery, pp. 1-16, 1988.
Malis, L., "The Value of Irrigation During Bipolar Coagulation" See ARTC 21602, 1 pg, Apr. 9, 1993.
Nardella, P.C., SPIE 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" Gastroenterology vol. 74(3), pp. 527-534, 1978.
Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.
Ramsey et al., "A Comparison of Bipolar and Monopolar Diathermy Probes in Experimental Animals", Urological Research vol. 13, pp. 99-102, 1985.
Selikowitz et al., "Electric Current and Voltage Recordings on the Myocardium During Electrosurgical Procedures in Canines," Surgery, Gynecology & Obstetrics, vol. 164, pp. 219-224, Mar. 1987.
Shuman, "Bipolar Versus Monopolar Electrosurgery: Clinical Applications," Dentistry Today, vol. 20, No. 12, 7 pgs, Dec. 2001.
Slager et al. "Spark Erosion of Arteriosclerotic Plaques" Z. Kardiol. 76:Suppl. 6, pp. 67-71, 1987.
Slager et al. "Vaporization of Atherosclerotice Plaques by Spark Erosion" JACC 5(6): pp. 1382-1386, Jun. 1985.
Stoffels, E. et al., "Investigation on the Interaction Plasma-Bone Tissue", E-MRS Spring Meeting, 1 pg, Jun. 18-22, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus Mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop", Nov. 1989.

Valley Forge Scientific Corp., "Summary of Safety and Effective Information from 510K", 2pgs, 1991.

Valley Forge's New Products, Clinica, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 2000.

PCT Notification of the International Search Report and Written Opinion for PCT/US07/69856, 7pgs, Mailed Jun. 5, 2008.

UK Search Report for GB0805062.7 1 pg, Jul. 16, 2008.

European Search Report for EP 02773432 3pgs, Dec. 19, 2008.

European Examination Report for EP 05024974 4 pgs, Dec. 5, 2008.

UK Search Report for GB0800129.9 2pgs, May 8, 2008.

European Search Report for EP 04708664.0 5pgs, Apr. 6, 2009.

UK Search Report for GB0900604.0 4 pgs, May 15, 2009.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endoscopic electrodes, and tissue," Gastrointestinal Endoscopy, vol. 38, No. 2, pp. 118-122, 1992.

European Examination Report for EP 02773432 4 pgs, Sep. 22, 2009.

European Examination Report for EP 04708664 7pgs, Sep. 7, 2009.

European Examination Report for EP 02749601.7 4pgs, Dec. 2, 2009.

European Examination Report 2 for EP 04708664 5pgs, May 3, 2010.

Extended European Search Report for EP09152846, 8pgs, Jan. 5, 2010.

European Search Report for EP 09152850, 2 pgs, Dec. 29, 2009.

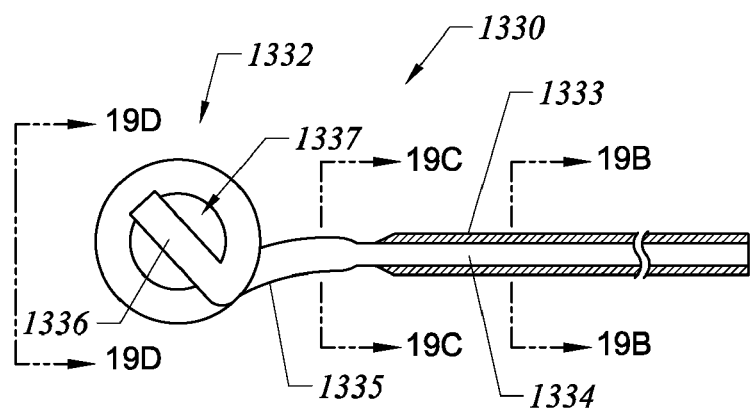
FIG. 19A
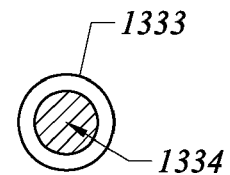
FIG. 19B
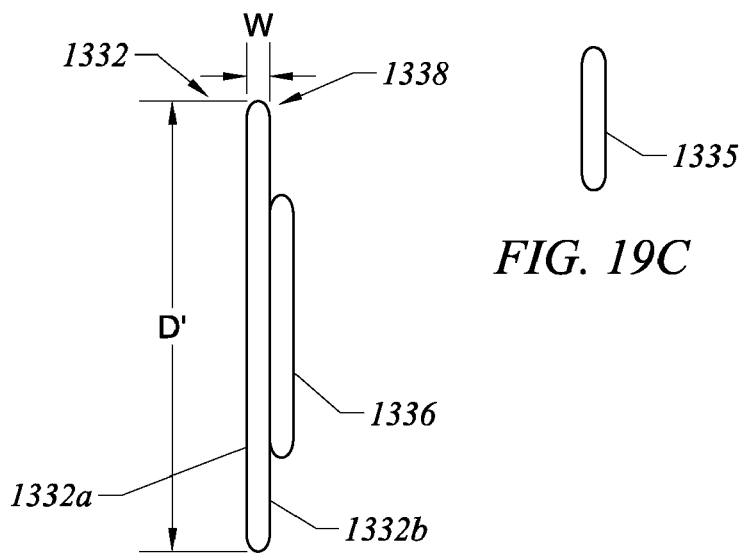
FIG. 19C
FIG. 19D

ELECTROSURGICAL APPARATUS AND METHODS FOR TREATMENT AND REMOVAL OF TISSUE

RELATED APPLICATIONS

The present application is a continuation of U.S. patent application Ser. No. 10/068,533 filed Feb. 5, 2002, now U.S. Pat. No. 7,270,661, which claims priority from U.S. Provisional Patent Application No. 60/299,094 filed Jun. 18, 2001 which is a continuation-in-part of U.S. patent application Ser. No. 09/586,295 filed Jun. 2, 2000, now U.S. Pat. No. 7,678, 069, which is a division of U.S. patent application Ser. No. 09/248,763 filed Feb. 12, 1999, now U.S. Pat. No. 6,149,620, which derives priority from U.S. Provisional Application Nos. 60/096,150 and 60/098,122, filed Aug. 11, 1998 and Aug. 27, 1998, respectively, and U.S. patent application Ser. No. 08/795,686, filed Feb. 5, 1997, now U.S. Pat. No. 5,871, 469, which is a continuation of U.S. patent application Ser. No. 08/561,958 filed Nov. 22, 1995, now U.S. Pat. No. 5,697, 882, the complete disclosures of which are incorporated herein by reference for all purposes.

The present invention is related to commonly assigned U.S. patent application Ser. No. 09/177,861, filed Oct. 23, 1998, now U.S. Pat. No. 6,066,134, application Ser. No. 08/977,845, filed Nov. 25, 1997, now U.S. Pat. No. 6,210, 402, which is a continuation-in-part of application Ser. No. 08/562,332, filed Nov. 22, 1995, now U.S. Pat. No. 6,024, 733, and U.S. patent application Ser. No. 09/010,382, filed Jan. 21, 1998, now U.S. Pat. No. 6,190,381, the complete disclosure of which is incorporated herein by reference. The present invention is also related to commonly assigned U.S. patent application Ser. No. 09/162,117, filed Sep. 28, 1998, now U.S. Pat. No. 6,117,109, and U.S. patent application Ser. No. 08/990,374, filed Dec. 15, 1997, now U.S. Pat. No. 6,109, 268, which is a continuation-in-part of U.S. patent application Ser. No. 08/485,219, filed on Jun. 7, 1995, now U.S. Pat. No. 5,697,281, patent application Ser. Nos. 09/109,219, filed on Jun. 30, 1998, 09/058,571, filed on Apr. 10, 1998, now U.S. Pat. No. 6,142,992, Ser. No. 08/874,173 filed on Jun. 13, 1997, now U.S. Pat. Nos. 6,179,824 and 09/002,315 filed on Jan. 2, 1998, now U.S. Pat. No. 6,183,469, and U.S. patent application Ser. No. 09/054,323, filed on Apr. 2, 1998, now U.S. Pat. No. 6,063,079, and U.S. patent application Ser. Nos. 09/032,375, filed Feb. 27, 1998, 08/942,580, filed on Oct. 2, 1997, now U.S. Pat. No. 6,159,194, U.S. application Ser. No. 08/753,227, filed on Nov. 22, 1996, now U.S. Pat. No. 5,873, 855, U.S. application Ser. No. 08/687,792, filed on Jul. 18, 1996, now U.S. Pat. No. 5,843,019, the complete disclosures of which are incorporated herein by reference for all purposes.

BACKGROUND OF THE INVENTION

The present invention relates generally to the field of electrosurgery and, more particularly, to surgical devices and methods which employ high frequency voltage to cut, ablate, treat, or modify body tissue.

Conventional electrosurgical methods are widely used since they generally reduce patient bleeding associated with tissue cutting operations and improve the surgeon's visibility. These traditional electrosurgical techniques for treatment have typically relied on thermal methods to rapidly heat and vaporize liquid within tissue and to cause cellular destruction. In conventional monopolar electrosurgery, for example, electric current is directed along a defined path from the exposed or active electrode through the patient's body to the return electrode, which is externally attached to a suitable location on the patient's skin. In addition, since the defined path through the patient's body has a relatively high electrical impedance, large voltage differences must typically be applied between the active and return electrodes to generate a current suitable for cutting or coagulation of the target tissue. This current, however, may inadvertently flow along localized pathways in the body having less impedance than the defined electrical path. This situation will substantially increase the current flowing through these paths, possibly causing damage to or destroying tissue along and surrounding this pathway.

Bipolar electrosurgical devices have an inherent advantage over monopolar devices because the return current path does not flow through the patient beyond the immediate site of application of the bipolar electrodes. In bipolar devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue.

Another limitation of conventional bipolar and monopolar electrosurgery devices is that they are not suitable for the precise removal (i.e., ablation) of tissue. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. The tissue is parted along the pathway of evaporated cellular fluid, inducing undesirable collateral tissue damage in regions surrounding the target tissue site.

The use of electrosurgical procedures (both monopolar and bipolar) in electrically conductive environments can be further problematic. For example, many arthroscopic procedures require flushing of the region to be treated with isotonic saline, both to maintain an isotonic environment and to keep the field of view clear. However, the presence of saline, which is a highly conductive electrolyte, can cause shorting of the active electrode(s) in conventional monopolar and bipolar electrosurgery. Such shorting causes unnecessary heating in the treatment environment and can further cause non-specific tissue destruction.

Conventional electrosurgical techniques used for tissue ablation also suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 µm, frequently greater than 800 µm, and sometimes as great as 1700 µm. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

In an effort to overcome at least some of these limitations of electrosurgery, laser apparatus have been developed for use in arthroscopic and other surgical procedures. Lasers do not suffer from electrical shorting in conductive environments, and certain types of lasers allow for very controlled cutting with limited depth of necrosis. Despite these advantages, laser devices suffer from their own set of deficiencies. In the first place, laser equipment can be very expensive because of the costs associated with the laser light sources. Moreover, those lasers which permit acceptable depths of necrosis (such as excimer lasers, erbium:YAG lasers, and the like) provide a very low volumetric ablation rate, which is a particular disadvantage in cutting and ablation of fibrocartilage, articular cartilage, and meniscal tissue. The holmium:YAG and Nd:YAG lasers provide much higher volumetric ablation rates, but are much less able to control depth of necrosis than are the slower laser devices. The $CO_2$ lasers provide high rate of ablation and low depth of tissue necrosis, but cannot operate in a liquid-filled cavity.

Excimer lasers, which operate in an ultraviolet wavelength, cause photo-dissociation of human tissue, commonly referred to as cold ablation. Through this mechanism, organic molecules can be disintegrated into light hydrocarbon gases that are removed from the target site. Such photo-dissociation reduces the likelihood of thermal damage to tissue outside of the target site. Although promising, excimer lasers must be operated in pulses so that ablation plumes created during operation can clear. This prevents excessive secondary heating of the plume of ablation products which can increase the likelihood of collateral tissue damage as well as a decrease in the rate of ablation. Unfortunately, the pulsed mode of operation reduces the volumetric ablation rate, which may increase the time spent in surgery.

Thus there is a need for apparatus and methods for effecting the controlled ablation, coagulation, or other modification of a target tissue in vivo, at a relatively low cost, and with no or minimal collateral tissue damage. The present invention provides such apparatus and methods, as is described in enabling detail hereinbelow.

SUMMARY OF THE INVENTION

The present invention provides systems, apparatus and methods for selectively applying electrical energy to body tissue.

In one embodiment, a method of the present invention comprises positioning an electrosurgical probe or catheter adjacent the target site so that one or more active electrode(s) are brought into contact with, or close proximity to, a target tissue in the presence of electrically conductive fluid. The electrically conductive fluid may be delivered directly to the active electrode(s) and the target tissue, or the entire target site may be submersed within the conductive fluid. High frequency voltage is then applied between the electrode terminal(s) and one or more return electrode(s) to generate a plasma adjacent to the active electrode(s), and to volumetrically remove or ablate at least a portion of the target tissue. The high frequency voltage generates electric fields around the active electrode(s) with sufficient energy to ionize the conductive fluid adjacent to the active electrode(s). Within the ionized gas or plasma, free electrons are accelerated, and electron-atoms collisions liberate more electrons, and the process cascades until the plasma contains sufficient energy to break apart the tissue molecules, causing molecular dissociation and ablation of the target tissue.

In some embodiments, the high frequency voltage applied to the electrode terminal(s) is sufficient to vaporize the electrically conductive fluid (e.g., gel or saline) between the electrode terminal(s) and the tissue. Within the vaporized fluid, a plasma is formed and charged particles (e.g., electrons) cause the molecular dissociation of several cell layers of the tissue. This molecular dissociation is accompanied by the volumetric removal of the tissue. This process can be precisely controlled to effect the volumetric removal of tissue as thin as 10 to 150 microns with minimal heating of, or damage to, surrounding or underlying tissue structures. A more complete description of this phenomenon is described in commonly assigned U.S. Pat. No. 5,697,882.

In some embodiments, the tissue is ablated by directly contacting the target tissue with the plasma. In other embodiments, the active electrode(s) are spaced from the tissue a sufficient distance to minimize or avoid contact between the tissue and the plasma formed around the active electrode(s). Applicant believes that the electrons that carry the electrical current contain more thermal energy than the ions within the plasma. In these embodiments, contact between the heated electrons in the plasma and the tissue is minimized as these electrons travel from the plasma back through the conductive fluid to the return electrode(s). The ions within the plasma will have sufficient energy, however, under certain conditions such as higher voltages, to accelerate beyond the plasma to the tissue. Thus, the electrons, which are carried away from the target tissue, carry most of the thermal byproducts of the plasma with them, allowing the ions to break apart the tissue molecules in a substantially non-thermal manner.

Apparatus according to the present invention generally includes an electrosurgical instrument having a shaft with proximal and distal ends, one or more active electrode(s) at the distal end and one or more connectors coupling the active electrode(s) to a source of high frequency electrical energy. In some embodiments, the instrument will comprise a catheter designed for percutaneous and/or transluminal delivery. In other embodiments, the instrument will comprise a more rigid probe designed for percutaneous or direct delivery in either open procedures or port access type procedures. In both embodiments, the apparatus will include a high frequency power supply for applying a high frequency voltage to the electrode terminal(s).

The apparatus may further include a supply or source of an electrically conductive fluid, and a fluid delivery element for delivering electrically conductive fluid to the electrode terminal(s) and the target site. The fluid delivery element may be located on the instrument, e.g., a fluid lumen or tube, or it may be part of a separate instrument. Alternatively, an electrically conductive gel or spray may be applied to the target site. In this embodiment, the apparatus may not have a fluid delivery element. In both embodiments, the electrically conductive fluid will preferably generate a current flow path between the active electrode(s) and one or more return electrode(s). In one embodiment, the return electrode is spaced a sufficient distance from the active electrode(s) to substantially avoid or minimize current shorting therebetween, and to shield the tissue at the target site from the return electrode.

The electrosurgical instrument may include an electrically insulating electrode support member or spacer, preferably an inorganic support material (e.g., ceramic, glass, glass/ceramic, etc.). The spacer separates the electrode terminal(s) from the return electrode. In one embodiment, the instrument includes an electrode array having a plurality of electrically isolated electrode terminals extending about 0.0 mm to about 10 mm distally from the distal end of the instrument. The probe may further include one or more lumens for delivering electrically conductive fluid and/or aspirating the target site.

In one configuration, the instrument includes a fluid delivery lumen for delivering electrically conductive fluid to the active and/or return electrodes, and an aspiration lumen for aspirating excess conductive fluid from the distal end of the apparatus or from the surgical site. In one embodiment, the fluid delivery and aspiration lumens create a fluid recirculation system for minimizing the amount of conductive fluid that contacts the patient, and for reducing the temperature to which a target tissue is exposed during a procedure.

According to another aspect of the invention, there is provided an electrosurgical probe including an active electrode having an active electrode head or terminal, and a return electrode having a return electrode head or terminal in the form of a coil. The return electrode coil usually comprises from about one (1) turn to fifty (50) turns, and more typically from about 3 to 10 turns. In one representative embodiment, the return electrode coil comprises about six turns. Typically, the return electrode coil is wound in a proximal direction, wherein the first turn of the coil is located at the distal end of the coil. Typically, the return electrode coil is located at the distal end of a shaft of the probe.

In an exemplary embodiment, a gap exists between each turn of the return electrode coil. The gaps between the turns of the return electrode coil facilitate wetting of the internal and external surfaces of the coil with an electrically conductive fluid delivered to the distal end of the shaft. The electrically conductive fluid delivered to the distal end of the shaft provides a current flow path between the active and return electrodes. The return electrode coil provides a relatively large surface area, and hence relatively low current densities, thereby decreasing the likelihood of inadvertent firing of the return electrode during treatment of a target tissue. Typically, the surface area of the return electrode coil is at least about twice (i.e., at least double, or 2×) the surface area of the active electrode head. More typically, the surface area of the return electrode coil is from about two times (2×) to about 20 times (20×) the surface area of the active electrode head. The active electrode head may be in the form of a hook, a metal disc, or a flattened coil.

In another aspect of the invention, there is provided an electrosurgical probe including an active electrode in the form of a flattened coil having from about 0.5 to 5 turns, preferably about 0.5 to 1.5 turns. In one embodiment, the active electrode includes a dividing portion disposed within an internal void of the active electrode coil, wherein the dividing portion at least partially spans the coil. In one embodiment, the dividing portion spans the coil of the active electrode, and divides the internal void within the coil into two portions. The presence of one or more voids within the coil promotes the retention of an electrically conductive fluid delivered to the coil. In one embodiment, the flattened coil has relatively sharp edges, which promote high current densities at the perimeter of the coil, thereby facilitating initiation and maintenance of a plasma in the presence of the electrically conductive fluid. The presence of a plasma at the perimeter of the active electrode coil promotes aggressive ablation and/or severing of target tissue via the molecular dissociation (vaporization) of tissue components.

According to another aspect of the invention, there is provided an electrosurgical probe including a multi-lumen shaft having a plurality of internal lumens. In one embodiment, the multi-lumen shaft includes four internal lumens, wherein a return electrode and an active electrode are accommodated within a first lumen and a second lumen, respectively; and wherein a third lumen and a fourth lumen comprise a fluid delivery lumen and an aspiration lumen, respectively. In an exemplary embodiment, the multi-lumen shaft comprises a plastic tube formed by an extrusion process, for example, by extrusion of a polyurethane elastomer.

According to another aspect, the invention provides an electrosurgical probe having a multi-lumen shaft and an electrode assembly disposed at the distal end of the shaft, wherein the electrode assembly includes a return electrode coil oriented substantially parallel to the shaft distal end. The electrode assembly further includes an active electrode having an active electrode head disposed at the distal end of an active electrode filament, wherein the active electrode filament passes within the return electrode coil. The active electrode head may comprise a flattened coil, the active electrode coil oriented substantially orthogonal to the return electrode coil. Typically, the surface area of the return electrode coil is from about two times to about 20 times the surface area of the active electrode head.

In another aspect of the invention, there is provided a method of forming a return electrode for an electrosurgical probe, wherein the method involves providing a length of return electrode wire, removing a layer of electrical insulation from a distal end portion of the wire, and wrapping the distal end portion of the wire to form a coil having from about 1 to 50 turns, preferably about 3 to 10 turns. Typically, the coil is wound in a proximal direction, and the distal terminus of the wire is arranged within an internal void defined by the coil.

According to another aspect, the invention provides a method of forming an active electrode for an electrosurgical probe, the method involving providing a length of active electrode wire, removing a layer of electrical insulation from a distal end of the wire, and wrapping the distal end of the wire to form a coil having from about 0.5 to 5 turns, preferably about 0.5 to 1.5 turns. Typically, the method further involves arranging a dividing portion within the coil, such that the dividing portion at least partially spans an internal void within the active electrode coil. After the active electrode coil, including the dividing portion, if any, has been formed, the active electrode coil may be flattened to form a substantially disc-like active electrode head, or flattened coil, having at least one void therein. Flattening the active electrode head provides a larger surface area for engaging a target tissue to be coagulated or ablated.

In another aspect of the invention, there is provided a method of ablating or modifying a target tissue of a patient, in vivo, using an electrosurgical probe. The probe may comprise a multi-lumen shaft, for example, a plastic tube formed by an extrusion process, a return electrode coil of from about 3 to 10 turns, and a flattened active electrode coil having from about 0.5 to 1.5 turns. The method involves positioning the active electrode coil in at least close proximity to the target tissue, delivering an electrically conductive fluid to the return electrode and/or the active electrode, and delivering a high frequency voltage between the active electrode and the return electrode from a high frequency power supply. The applied voltage is sufficient to ablate or modify the target tissue. During application of the high frequency voltage, the active electrode coil may be translated, e.g., in the plane of the active electrode coil to effect cutting or severing of the target tissue, or orthogonal to the plane of the active electrode coil to effect volumetric removal of the tissue.

For a further understanding of the nature and advantages of the invention, reference should be made to the following description taken in conjunction with the accompanying drawings.

BRIEF DESCRIPTION OF THE DRAWINGS

FIGS. 19A-D illustrate an active electrode having a flattened coil, according to another embodiment of the invention;

DESCRIPTION OF SPECIFIC EMBODIMENTS

Figure 1:
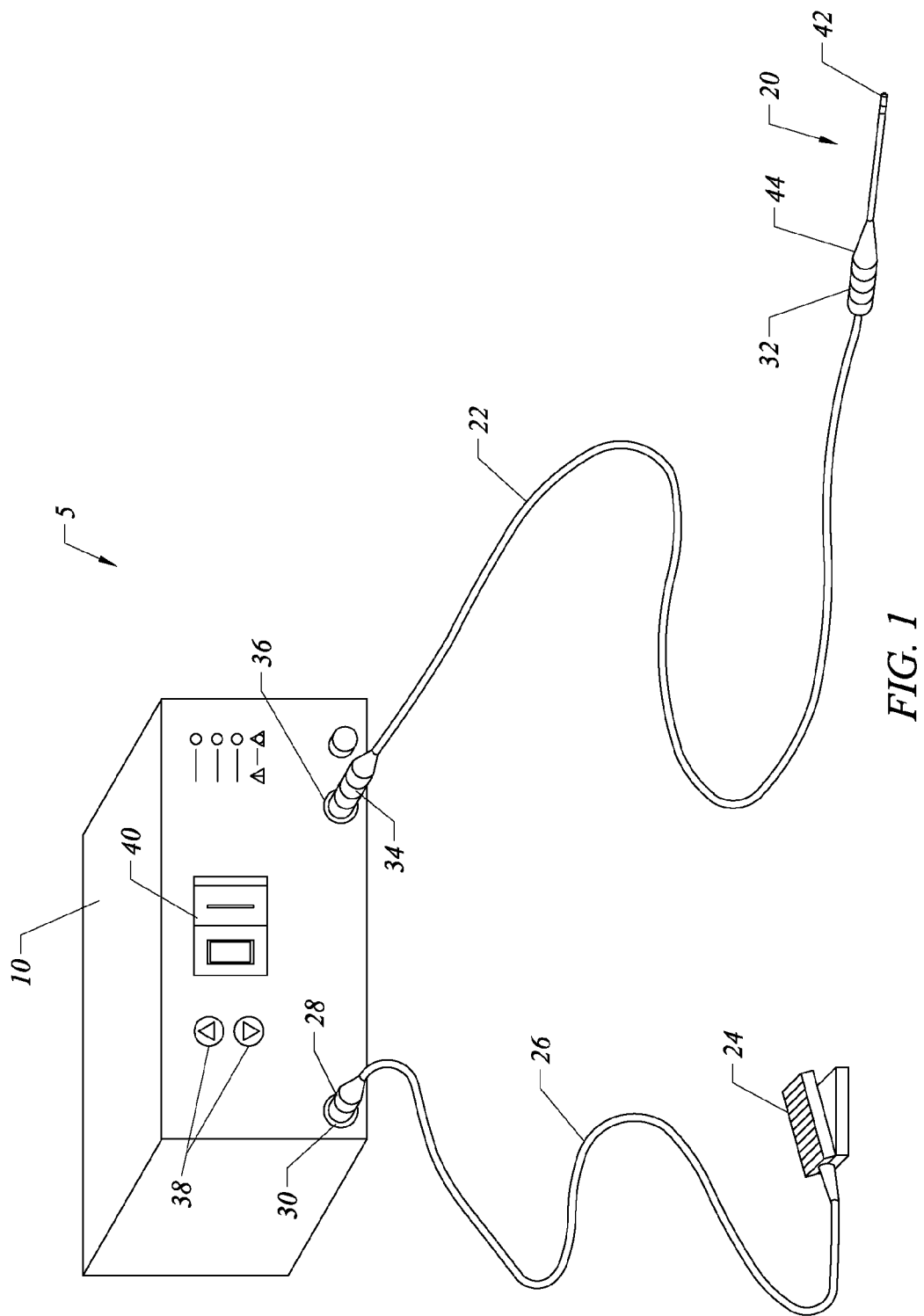
FIG. 1 is a perspective view of an electrosurgical system incorporating a power supply and an electrosurgical probe, according to the invention.

In the present invention, high frequency (RF) electrical energy is applied to one or more electrode terminals in the presence of electrically conductive fluid to remove and/or modify body tissue. The techniques of the present invention may be performed in a conventional open surgery environment or in a minimally invasive manner using cannulas, or port access devices. The present invention is useful in procedures where the tissue site is flooded or submerged with an electrically conductive fluid, such as arthroscopic surgery of the knee, shoulder, ankle, hip, elbow, hand or foot. Specifically, the present invention is useful in the resection and/or ablation of the meniscus and the synovial tissue within a joint during an arthroscopic procedure. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye, or epidermal and dermal tissues on the surface of the skin. The present invention is also useful for resecting tissue within accessible sites of the body that are suitable for electrode loop resection, such as the resection of prostate tissue, leiomyomas (fibroids) located within the uterus, and other diseased tissue within the body.

The present invention is also useful for treating tissue in the head and neck, such as the ear, mouth, pharynx, larynx, esophagus, nasal cavity and sinuses. The head and neck procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps, turbinates and/or neoplasms from the various anatomical sinuses of the skull, the turbinates and nasal passages, in the tonsil, adenoid, epi-glottic and supra-glottic regions, and salivary glands, submucous resection of the nasal septum, excision of diseased tissue and the like. In other procedures, the present invention may be useful for collagen shrinkage, ablation and/or hemostasis in procedures for treating swollen tissue (e.g., turbinates) or snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of brain tumors, facial tumors, or tumors within the mouth and pharynx. In addition, the present invention is useful for procedures within the ear, such as stapedotomies, tympanostomies or the like.

The present invention may also be useful for treating tissue of the brain and vertebral column. These procedures include tumor removal, laminectomy/disketomy procedures for treating herniated disks, decompressive laminectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar diskectomies. These procedures may be performed through open procedures, or using minimally invasive techniques, such as thoracoscopy, arthroscopy, laparascopy or the like.

The present invention may also be useful for cosmetic and plastic surgery procedures in the head and neck. For example, the present invention is useful for ablation and sculpting cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

The systems, apparatus, and methods of the invention are applicable to a broad range of procedures including, without limitation: open procedures, intravascular procedures, interventional cardiology procedures, urology, laparascopy, arthroscopy, thoracoscopic or other cardiac procedures, cosmetic surgery, orthopedics, gynecology, otorhinolaryngology, spinal and neurologic procedures, oncology and the like.

In one aspect of the invention, the body tissue is volumetrically removed or ablated. In this procedure, a high frequency voltage difference is applied between one or more electrode terminal(s) and one or more return electrode(s) to develop high electric field intensities in the vicinity of the target tissue. The high electric field intensities adjacent the electrode terminal(s) lead to electric field induced molecular breakdown of target tissue via molecular dissociation (as opposed to thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation.

The high electric field intensities may be generated by applying a high frequency voltage that is sufficient to vaporize an electrically conductive fluid over at least a portion of the electrode terminal(s) in the region between the distal tip of the electrode terminal(s) and the target tissue. The electrically conductive fluid may be a liquid, such as isotonic saline or blood, delivered to the target site, a viscous fluid, such as a gel, or a gas. Since the vapor layer or vaporized region has a relatively high electrical impedance, it minimizes the current flow into the electrically conductive fluid). This ionization, under the conditions described herein, induces the discharge of energetic electrons and photons from the vapor layer and to the surface of the target tissue. A more detailed description of this process, termed Coblation™ can be found in commonly assigned U.S. Pat. No. 5,697,882, the complete disclosure of which is incorporated herein by reference.

Applicant believes that the principal mechanism of tissue removal in the Coblation™ process of the present invention is via the action of charged particles (e.g., energetic electrons) that have been energized in a plasma adjacent to the electrode terminal(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a small volume of gas and ionizing the gas by driving an electric current through it, or by transmitting radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

Applicant has found that increasing the current densities around the electrode terminal(s) can lead to higher energy levels in the ionized plasma. This, in turn, allows the ionized plasma to break stronger molecular bonds, such as those present in bone or calcified fragments. Since the electrically conductive fluid between the target site and electrode terminal(s) is transformed into an ionized vapor layer or plasma, the number of charged particles which can be accelerated against the target also determines the ablation rate. In addition, the conductivity of the fluid may have an effect on the strength of the plasma field created at the end of the probe. Typically, isotonic saline with a concentration of 0.9% sodium chloride is used with the probe. In some embodiments, increasing the sodium chloride concentration to greater than 0.9%, and perhaps between about 3% and 20%, may lead to increased rates of tissue ablation. This concept of using a hypertonic saline solution with enhanced conductivity and increased numbers of charged particles is of particular use in bone removal processes or in other procedures requiring aggressive volumetric removal.

Applicant has also found that the plasma layer typically requires a higher voltage level to initiate a plasma than to sustain the plasma once it has been initiated. In addition, it has been found that some conductive solutions facilitate the initiation of the plasma layer, rather than the energy level of the plasma, as discussed above. For example, it has been found that saline solutions having concentrations less than isotonic saline (i.e., less than 0.9% sodium chloride) facilitate the initiation of the plasma layer. This may be useful in applications where initiation of the plasma layer is more difficult, such as applications where a suction pressure is applied near the electrode terminal(s). A more complete description of this type of application, and the devices that carry out simultaneous suction and ablation can be found in U.S. patent application Ser. No. 09/010,382, filed Jan. 21, 1998, the complete disclosure of which is incorporated herein by reference for all purposes.

In some embodiments, the present invention applies high frequency (RF) electrical energy in an electrically conductive fluid environment to remove (i.e., resect, cut or ablate) a tissue structure and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a sub-ablation mode, wherein a second, lower voltage is applied to an electrode terminal (either the same or a different electrode) sufficient to achieve non-ablative treatment of tissue, e.g., shrinkage of tissue, coagulation or hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue, or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal(s). In other embodiments, the power supply is combined with the electrosurgical instrument such that the coagulation electrode is used when the power supply is in the coagulation mode (low voltage), and the electrode terminal(s) are used when the power supply is in the ablation mode (higher voltage). In other embodiments, an electrosurgical instrument is provided having a single active electrode adapted for cutting, volumetrically removing, shrinking, and coagulating a target tissue. In these embodiments, the nature of the tissue treatment or effect depends on, among other factorsgeometry and configuration of the active and return electrodes, the type of tissue at the treatment site, the manner in which the active electrode is manipulated with respect to the tissue, and/or the voltage applied from the power supply (e.g., in the ablation mode or the sub-ablation mode) Manipulation of an electrosurgical probe to effect different types of tissue treatment are discussed hereinbelow.

In one method of the present invention, one or more electrode terminals are brought into at least close proximity to a target tissue, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation (sub-ablation) mode. In the sub-ablation mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The present invention is also useful for removing or ablating tissue around nerves, such as spinal, or cranial nerves, e.g., optic nerve, facial nerves, vestibulocochlear nerves and the like. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves around the target site. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty material having substantially different electrical properties than "normal" target tissue. The system of the present invention measures the electrical properties of the tissue at the tip of the probe with one or more sensing electrodes. These electrical properties may include electrical conductivity at one, several or a range of frequencies (e.g., in the range of from 1 kHz to 100 MHz), dielectric constant, capacitance, or combinations of these. In this embodiment, an audible signal may be produced when the sensing electrode(s) at the tip of the probe detects the fatty material surrounding a nerve, or direct feedback control can be provided to supply power to the electrode terminal(s), either individually or to the complete array of electrodes, only if and when the tissue encountered at the working end of the probe is normal tissue based on the measured electrical properties.

In one embodiment, the current limiting elements (discussed in detail above) are configured such that individual electrode terminals in an electrode array will shut down or turn off when the electrical impedance reaches a threshold level. When this threshold level is set to the impedance of the fatty material surrounding peripheral nerves, the electrode terminals will shut off whenever they come in contact with, or in close proximity to, nerves. Meanwhile, other electrode terminals, which are in contact with or in close proximity to normal target tissue, will continue to conduct electric current to the return electrode. This selective ablation or removal of lower impedance tissue, in combination with the Coblation™ mechanism of the present invention, allows the surgeon to precisely remove tissue around nerves or bone. Applicant has found that the present invention is capable of volumetrically removing tissue closely adjacent to nerves without impairing the function of the nerves, and without significantly damaging the tissue of the epineurium. In the present invention, the Coblation™ process for removing tissue results in extremely small depths of collateral tissue damage as discussed above. This allows the surgeon to remove tissue close to a nerve without causing collateral damage to the nerve fibers.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose tissue) has double bonds that require a substantially higher energy level than 4 to 5 eV to break. Accordingly, the present invention in its current configuration generally does not ablate or remove such fatty tissue. However, the present invention may be effectively used to release the inner fat content in a liquid form. Of course, factors may be changed such that these double bonds can also be broken in a similar fashion as the single bonds (e.g., increasing the voltage, or changing the electrode configuration to increase the current density at the electrode tips). A more complete description of this phenomenon can be found in co-pending U.S. patent application Ser. No. 09/032,375, filed Feb. 27, 1998, the complete disclosure of which is incorporated herein by reference.

The present invention also provides systems, apparatus and methods for selectively removing tumors, e.g., brain tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacteria, cells, or viral particles from the tumor or lesion to the surgical team or to other portions of the patient's body. This potential spread of viable bacteria, cells, or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tumor tissue via the molecular dissociation of tissue components into non-viable atoms and molecules. Specifically, the present invention converts the solid tissue into non-condensable gases that are no longer intact or viable, and thus, incapable of spreading viable tumor cells or infectious particles to other parts of the patient's body or to the surgical staff. The high frequency voltage is preferably selected to effect controlled removal of these tissue cells while minimizing or avoiding substantial tissue necrosis to surrounding or underlying tissue. A more complete description of this phenomenon can be found in co-pending U.S. patent application Ser. No. 09/109,219, filed Jun. 30, 1998, the complete disclosure of which is incorporated herein by reference.

In one embodiment, an electrosurgical instrument comprises a shaft having a proximal end and a distal end which supports one or more electrode terminal(s). The shaft may assume a wide variety of configurations, with the primary purpose being to mechanically support one or more electrode terminal(s) and permit the treating physician to manipulate the electrode(s) from a proximal end of the shaft. Usually, an electrosurgical probe shaft will be a narrow-diameter rod or tube, more usually having dimensions which permit it to be introduced through a cannula into the patient's body. Thus, the probe shaft will typically have a length of at least 5 cm for open procedures and at least 10 cm, more typically being 20 cm, or longer for endoscopic procedures. The probe shaft will typically have a diameter of at least 1 mm, and frequently in the range from 1 mm to 10 mm. For dermatology or other procedures on the skin surface, the shaft will have any suitable length and diameter that would facilitate handling by the surgeon.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The instrument shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The instrument shaft will usually include a plurality of wires or other conductive elements running axially therethrough to permit connection of the electrode or electrode array and the return electrode to a connection block at the proximal end of the shaft. In one embodiment, the shaft may include a rigid multi-lumen tube, wherein a return electrode lead or filament occupies a first lumen, and an active electrode lead or filament occupies a second lumen. In another embodiment, the shaft may include a guide wire for guiding the catheter to the target site, or the instrument may comprise a steerable guide catheter. A catheter of the invention may also include a substantially rigid distal end portion to increase the torque control of the distal end portion as the catheter is advanced further into the patient's body. Specific shaft designs will be described in detail in connection with the figures hereinafter.

The electrode terminal(s) may be supported by, or partially surrounded by an electrically insulating electrode support or spacer positioned at or near the distal end of the instrument shaft. The return electrode may be located at the shaft distal end, on a separate instrument, or on the external surface of the patient (i.e., a dispersive pad). In most applications, applicant has found that it is preferably to have the return electrode on or near the shaft of the instrument to confine the electric currents to the target site. In some applications and under certain conditions, however, the invention may be practiced in a monopolar mode, with the return electrode attached to the external surface of the patient. Accordingly, the return electrode is preferably either integrated with the instrument shaft, or integral with a separate instrument located in close proximity to the distal end of the instrument shaft. The proximal end of the instrument will include the appropriate electrical connections for coupling the return electrode(s) and the electrode terminal(s) to a high frequency power supply, such as an electrosurgical generator or power supply. In one embodiment, the return electrode comprises a distal portion in the form of a coil, and a proximal filament arranged within the shaft and coupled to a connection block housed within a handle of the instrument.

The current flow path between the electrode terminals and the return electrode(s) may be generated by submerging the tissue site in an electrically conductive fluid (e.g., within a viscous fluid, such as an electrically conductive gel), or by directing an electrically conductive fluid along a fluid path to the target site (i.e., a liquid, such as isotonic saline, hypotonic saline; or a gas, such as argon). The conductive gel may also be delivered to the target site to achieve a slower more controlled delivery rate of electrically conductive fluid. In addition, the viscous nature of the gel may allow the surgeon to more easily contain the gel around the target site (e.g., rather than attempting to contain isotonic saline). A more complete description of an exemplary method of directing electrically conductive fluid between the active and return electrodes is described in U.S. Pat. No. 5,697,281, the contents of which are incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply or electrosurgical generator may include a fluid interlock for interrupting power to the electrode terminal(s) when there is insufficient conductive fluid around the electrode terminal(s). This ensures that the instrument will not be activated when conductive fluid is not present, minimizing the tissue damage that may otherwise occur. A more complete description of such a fluid interlock can be found in commonly assigned, U.S. patent application Ser. No. 09/058,336, filed Apr. 10, 1998, the complete disclosure of which is incorporated herein by reference.

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on a separate instrument, coupled to a suitable vacuum source for aspirating excess fluids or unwanted materials from the target site. In addition, the invention may include one or more aspiration electrode(s) for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode(s) can be found in commonly assigned U.S. patent application Ser. No. 09/010,382 filed Jan. 21, 1998, now U.S. Pat. No. 6,190,381, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting, or otherwise modifying the target tissue. The tissue volume over which energy is dissipated (i.e., over which a high current density exists) may be more precisely controlled, for example, by the use of a multiplicity of small electrode terminals whose effective diameters or principal dimensions range from about 10 mm to 0.01 mm, preferably from about 2 mm to 0.05 mm, and more preferably from about 1 mm to 0.1 mm. Electrode areas for both circular and non-circular terminals will have a contact area (per electrode terminal) below 50 mm$^2$ for electrode arrays and as large as 75 mm$^2$ for single electrode embodiments. In multiple electrode arrays, the contact area of each electrode terminal is typically in the range from 0.0001 mm$^2$ to 1.0 mm$^2$, and more preferably from 0.001 mm$^2$ to 0.5 mm$^2$. The circumscribed area of the electrode array or electrode terminal is in the range from 0.25 mm$^2$ to 75 mm$^2$, preferably from 0.5 mm$^2$ to 40 mm$^2$.

The distal or working end of the instrument, including the active and return electrodes, can assume a variety of geometries, with particular geometries and configurations being selected for specific applications. Typically, the active electrode(s) or electrode terminal(s) are located at the distal tip of the electrosurgical instrument. Alternatively or additionally, the active electrode(s) may be formed on lateral surfaces of the electrosurgical instrument shaft, e.g., for facilitating access to certain body structures during endoscopic procedures.

The electrically conductive fluid should have an electrical conductivity above a minimum threshold level to provide a suitable current flow path between the return electrode and the electrode terminal(s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium, and the like. In addition, other electronegative elements may be used in place of chlorine, such as fluorine.

The voltage difference applied between the return electrode(s) and the electrode terminal(s) will be at high or radio frequency (RF), typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400 to 600 kHz) in order to minimize low frequency current flow into the heart or the nerves of the head and neck. The RMS (root mean square) voltage applied will usually be in the range of from about 5 volts RMS to 1000 volts RMS, typically being in the range from about 10 volts RMS to 500 volts RMS, and often between about 150 volts RMS to 350 volts RMS, depending on the electrode terminal size, the operating frequency, and the operation mode of the particular procedure, or desired effect on the tissue (e.g., contraction, coagulation, cutting or ablation). Typically, the peak-to-peak voltage for ablation or cutting with a square wave form will be in the range of from about 10 to 2000 volts, preferably in the range of 100 to 1800 volts, and more preferably in the range of about 300 to 1500 volts, often in the range of about 300 to 800 volts peak to peak (again, depending on the electrode size, the operating frequency, and the operation mode). Lower peak-to-peak voltages may be used for tissue coagulation or collagen contraction, and will typically be in the range of from about 50 to 1500, preferably 100 to 1000, and more preferably 120 to 400 volts peak-to-peak (again, these values are computed using a square wave form). Higher peak-to-peak voltages, e.g., greater than about 700 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed at about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular procedure, e.g., neurosurgery, cardiac surgery, arthroscopic surgery, dermatological procedure, ophthalmic procedures, open surgery, or various endoscopic surgical procedures. For cardiac procedures, and potentially for neurosurgery, the power source may have an additional filter, for filtering leakage voltages at frequencies below about 100 kHz, particularly voltages around 60 kHz. Alternatively, a power source having a higher operating frequency, e.g., from about 300 to 600 kHz may be used in certain procedures in which stray low frequency currents may be problematic. A description of one suitable power source can be found in co-pending patent application Ser. Nos. 09/058,571 and 09/058,336, filed Apr. 10, 1998, the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 μH to 50,000 μH, depending on the electrical properties of the target tissue, the desired tissue heating rate, and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

In one embodiment, the instrument incorporates a single active electrode that extends directly through the shaft and is connected by a single lead or filament to a connection block that is adapted for facile coupling to a high frequency power supply. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like. In an exemplary embodiment, the active electrode comprises a flattened electrode head, e.g., in the form of a flattened 1-turn coil, or a disc.

In one embodiment, an electrosurgical catheter or probe comprises a single active electrode terminal encircled along a portion of its length by an electrically insulating spacer, e.g., comprising a ceramic. The insulating member may be a tubular or cylindrical structure that separates the active electrode terminal from a distal portion of the return electrode, the return electrode lying external to the insulating spacer.

The current flow path between the electrode terminal(s) and the return electrode(s) may be generated by submerging the tissue site in an electrically conductive fluid (e.g., within a viscous fluid, such as an electrically conductive gel) or by directing an electrically conductive fluid along a fluid path to the return electrode and/or the active electrode. This latter method is particularly effective in a dry environment (i.e., the tissue is not submerged in fluid) because the electrically conductive fluid provides a suitable current flow path from the active electrode head or terminal to the return electrode.

Referring to FIG. 1, an exemplary electrosurgical system 5 for treatment of tissue in the body will now be described in detail. As shown, electrosurgical system 5 generally includes an electrosurgical probe 20 connected to a power supply 10 for providing high frequency voltage to one or more electrode terminals 42 on probe 20. Probe 20 includes a connector housing 44 at its proximal end, which can be removably connected to a probe receptacle 32 of a probe cable 22. The proximal portion of cable 22 has a connector 34 to couple probe 20 to power supply 10. Power supply 10 has an operator controllable voltage level adjustment 38 to change the applied voltage level, which is observable at a voltage level display 40. Power supply 10 also includes one or more foot pedal(s) 24 and one or more cable(s) 26 which are each removably coupled to receptacle 30 with a cable connector 28. The foot pedal(s) 24 may include a second pedal (not shown) for remotely adjusting the energy level applied to electrode terminals 42, and a third pedal (also not shown) for switching between an ablation mode and a sub-ablation mode (e.g., for coagulation or contraction of tissue).

In one embodiment, a first foot pedal is used to place the power supply into the ablation mode and a second foot pedal (not shown) places power supply 10 into the sub-ablation mode. A third foot pedal (not shown) allows the user to adjust the voltage level within the ablation mode. In the ablation mode, a sufficient voltage is applied to the electrode terminals to establish the requisite conditions for molecular dissociation of the tissue. As discussed above, the requisite voltage level for ablation will vary depending on the number, size, shape and spacing of the electrodes, and the distance to which the electrodes extend from the probe distal end. When the surgeon is using the power supply in the ablation mode, voltage level adjustment 38 or the third foot pedal may be used to adjust the voltage level to adjust the degree or aggressiveness of the ablation. Of course, it will be recognized that the voltage and modality of the power supply may also be controlled by other input devices.

In the sub-ablation mode, power supply 10 applies a low enough voltage to one or more electrode terminals (or one or more coagulation electrodes) to avoid vaporization of the electrically conductive fluid, formation of a plasma, and subsequent molecular dissociation of the tissue. The surgeon may automatically toggle the power supply between the ablation and sub-ablation modes by alternatively stepping on the appropriate foot pedals. This allows the surgeon to quickly move between coagulation and ablation in situ, without having to remove his/her concentration from the surgical field, or without having to request an assistant to switch the power supply. By way of example, as the surgeon is treating soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply actuate the appropriate foot pedal, automatically lowering the voltage level below the threshold level for ablation, and apply sufficient pressure onto the severed vessel for a sufficient period of time to seal and/or coagulate the vessel. After hemostasis is achieved, the surgeon may quickly move back into the ablation mode by actuating the appropriate foot pedal. A specific design of a suitable power supply for use with the present invention can be found in U.S. patent application Ser. No. 09/058,571, filed Apr. 10, 1998, now U.S. Pat. No. 6,142,992, the contents of which are incorporated herein by reference.

Figure 2:
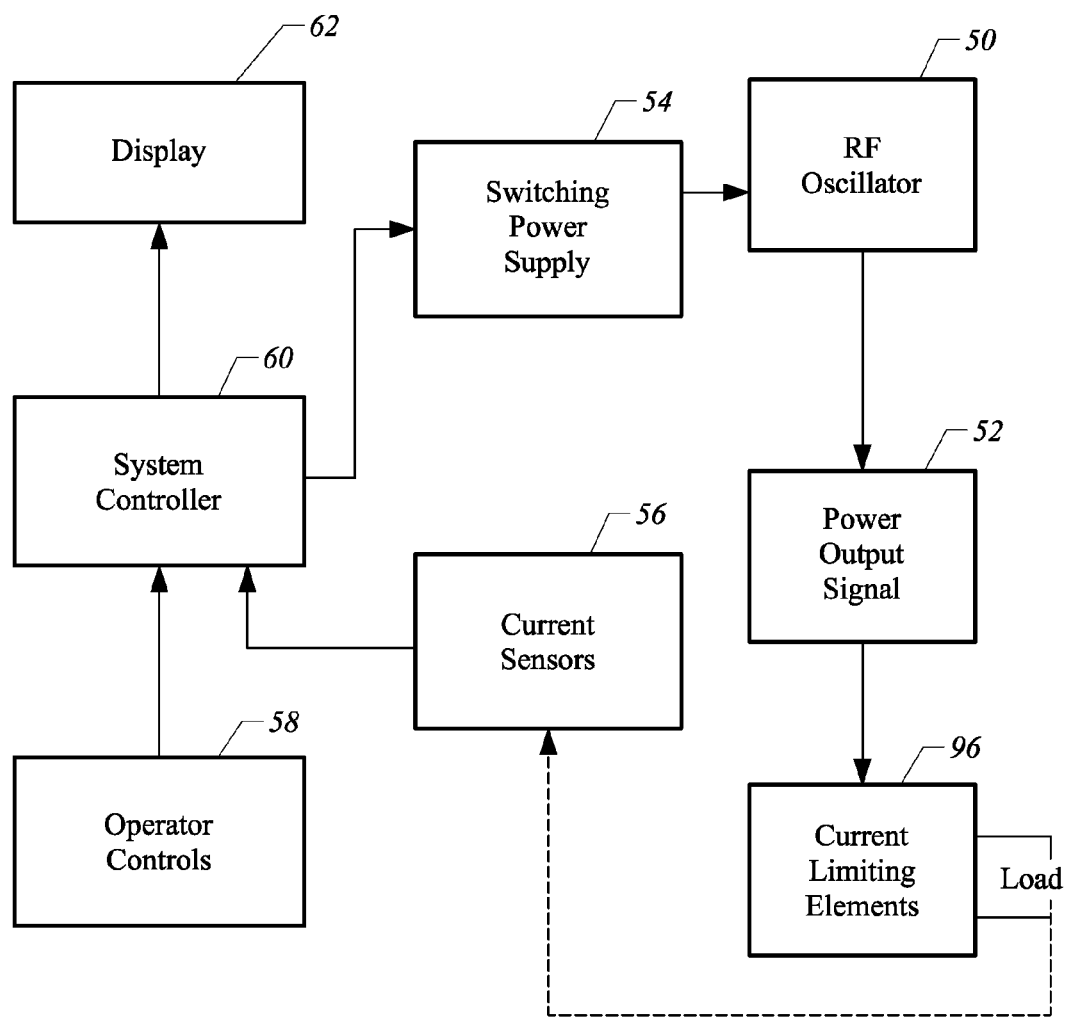
FIG. 2 schematically illustrates one embodiment of a power supply, according to the present invention.
Figure 3:
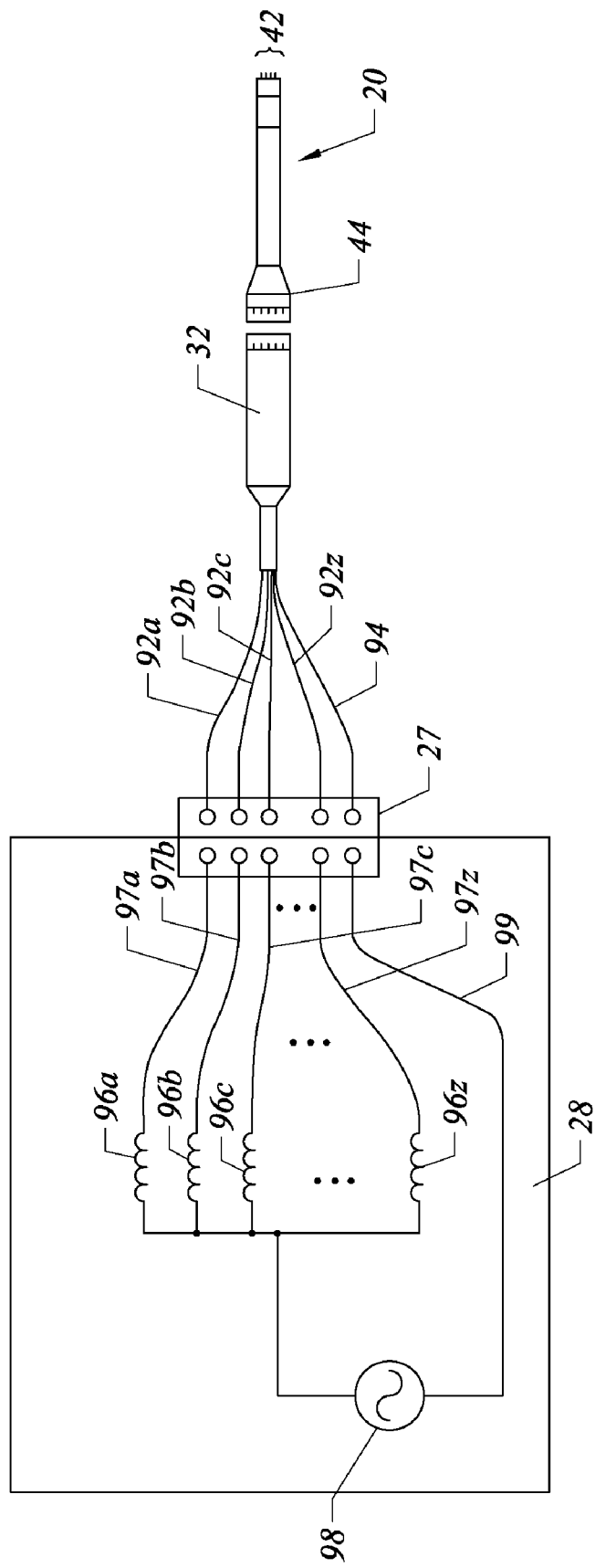
FIG. 3 illustrates an electrosurgical system incorporating a plurality of active electrodes and associated current limiting elements.

Referring now to FIGS. 2 and 3, a representative high frequency power supply or generator for use according to the principles of the present invention will now be described. The high frequency power supply of the present invention is configured to apply a high frequency voltage of from about 10 volts RMS to 500 volts RMS between one or more electrode terminals (and/or coagulation electrode) and one or more return electrodes. In the exemplary embodiment, the power supply applies from about 70 volts RMS to 500 volts RMS in the ablation mode, and from about 10 volts RMS to 90 volts RMS in the sub-ablation mode, preferably from about 45 to 70 volts RMS in the sub-ablation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being treated, and/or the maximum allowed temperature selected for the probe tip. The power source allows the user to select the voltage level according to the specific requirements of a particular procedure, e.g., arthroscopic surgery, dermatological procedure, ophthalmic procedures, open surgery, or other endoscopic surgery procedure.

As shown in FIG. 2, the power supply or generator generally comprises a radio frequency (RF) power oscillator 50 having output connections for coupling via a power output signal 52 to the load impedance, which is represented by the electrode assembly when the electrosurgical probe is in use. In the representative embodiment, the RF oscillator operates at about 100 kHz. The RF oscillator is not limited to this frequency and may operate at frequencies of from about 300 kHz to 600 kHz. In particular, for cardiac applications, the RF oscillator will preferably operate in the range of from about 400 kHz to 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 52 is designed to incur minimal voltage decrease (i.e., sag) under load. This improves the applied voltage to the electrode terminals and the return electrode, which improves the rate of volumetric removal (ablation) of tissue.

Power is supplied to the oscillator 50 by a switching power supply 54 coupled between the power line and RF oscillator 50 rather than a conventional transformer. The switching power supply 54 allows the generator to achieve high peak power output without the large size and weight of a bulky transformer. The architecture of switching power supply 54 has also been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 54 operates at about 100 kHz.

A system controller 60, coupled to the operator controls 58 (e.g., foot pedals and hand-actuated voltage selector) and a display 62, is connected to a control input of switching power supply 54 for adjusting the generator output power by supply voltage variation. System controller 60 may be a microprocessor or an integrated circuit. The generator may also include one or more current sensors 56 for detecting the output current. The generator is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The generator generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors, and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 µH, usually about 300 µH, for each of the channels supplying current to the electrode terminals (see FIG. 3).

Alternatively, in one embodiment, current limiting inductors are placed in series with each independent electrode terminal, where the inductance of the inductor is in the range of 10 µH to 50,000 µH, depending on the electrical properties of the target tissue, the desired tissue heating rate, and the operating frequency. Alternatively, capacitor-inductor (LC) circuit structures may be employed, as described previously in PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from the electrode terminal into the low resistance medium (e.g., saline irrigant or conductive gel). Power output signal 52 may also be coupled to a plurality of current limiting elements 96, which are preferably located on the daughter board since the current limiting elements may vary depending on the application.

FIG. 3 illustrates an arrangement that may be used in various electrosurgical procedures with a multi-electrode probe. As shown, a high frequency power supply 28 comprises a voltage source 98 which is connected to a multiplicity of current limiting elements 96a, 96b, . . . 96z, typically being inductors having an inductance in the range of about 100 to 5000 µH, with the particular value depending on the electrode terminal dimensions, the desired ablation rates, and the like. Capacitors having capacitance values in the range of about 200 to 10,000 picofarads may also be used as the current limiting elements. It would also be possible to use resistors as current limiting elements. The current limiting elements may also be part of a resonant circuit structure, as described in detail in PCT Application No. PCT/US94/05168, the contents of which are incorporated herein by reference.

Figure 4:
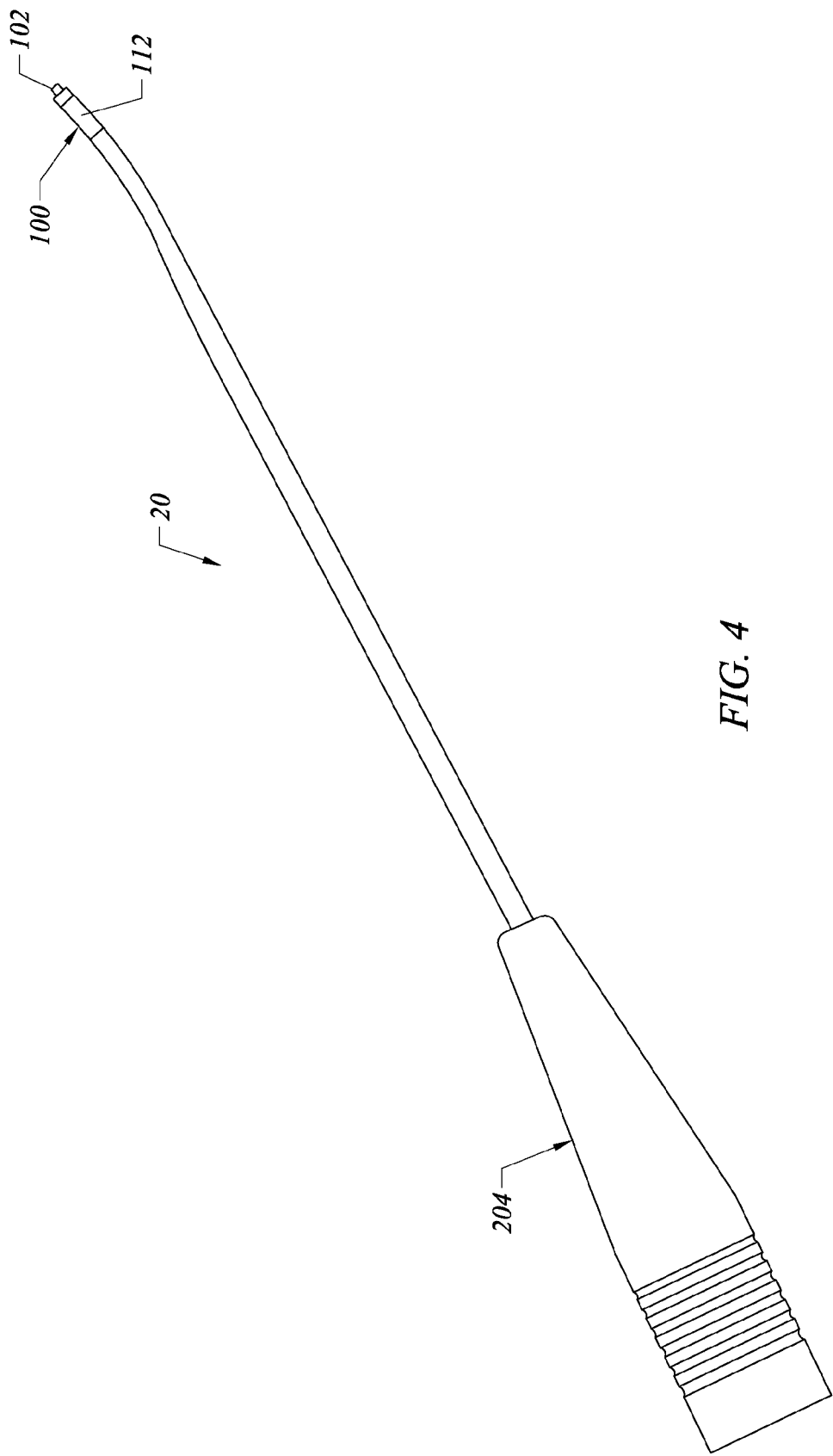
FIG. 4 is a side view of an electrosurgical probe according to the present invention.

FIG. 4 illustrates a probe 20, which generally includes an elongated shaft 100, a handle 204 coupled to the proximal end of shaft 100, and an electrode support member or spacer 102 coupled to the distal end of shaft 100. In the embodiment shown in FIG. 4, electrode support member 102 extends from the distal end of shaft 100 (usually by about 1 mm to 20 mm), and provides support for one or more electrically isolated electrode terminals (not shown in FIG. 4). Electrode support member 102 is typically a silicone rubber, a ceramic, a glass, or a glass/ceramic composition (e.g., aluminum oxide, titanium nitride, or the like). Alternatively, electrode support member 102 may comprise a high-temperature biocompatible plastic, such as polyether-ether-ketone (PEEK) (Vitrex International Products, Inc.), or polysulfone (GE Plastics). A return electrode 112 is located proximal to support member 102.

Figure 5:
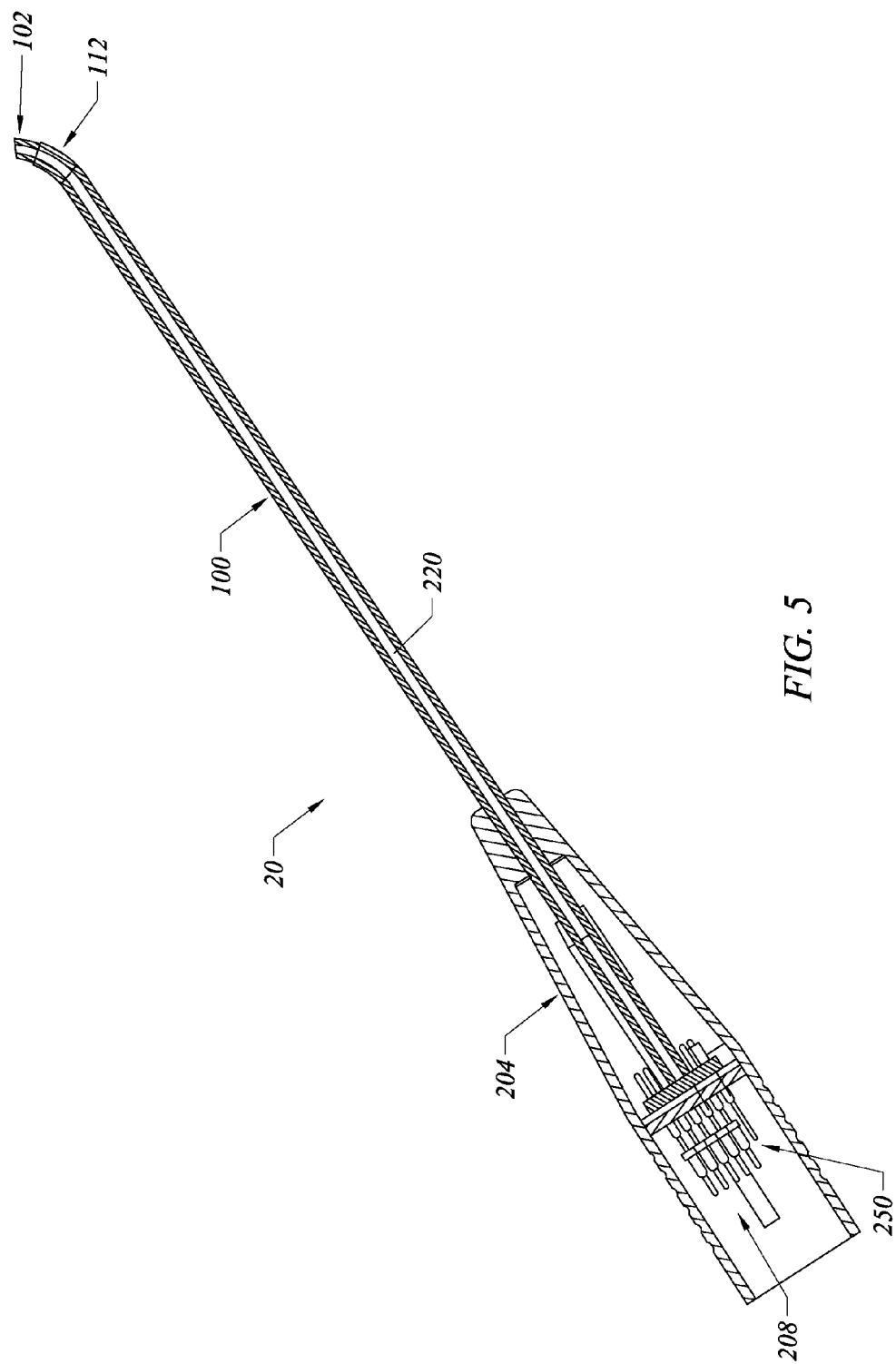
FIGS. 5-8 illustrates an alternative probe incorporating an aspiration lumen, according to the present invention.
Figure 7:
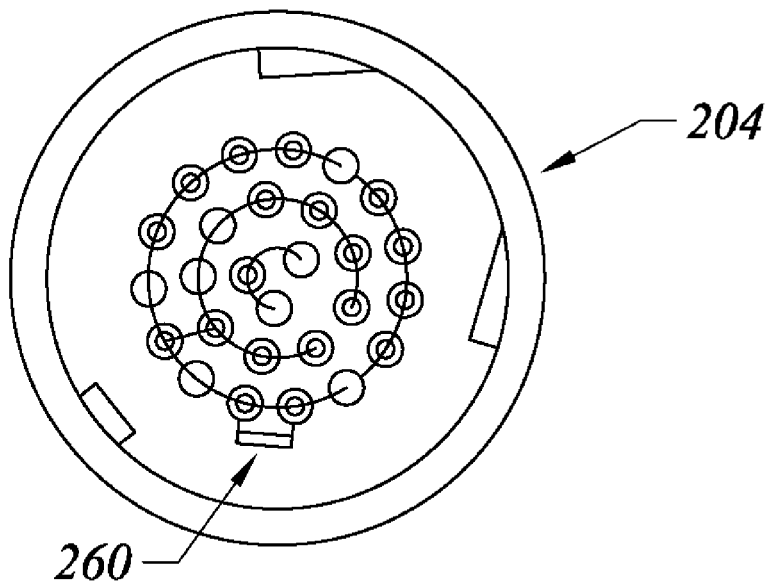

Handle 204 typically comprises a plastic material that is easily molded into a suitable shape for handling by the surgeon. As shown in FIG. 5, handle 204 defines an inner cavity 208 that houses the electrical connections 250, and provides a suitable interface for coupling probe 20 to an electrical connecting cable 22 (see FIG. 1). As shown in FIG. 7, the probe will typically include a coding resistor 260 having a value selected to program different output ranges and modes of operation for the power supply. This allows a single power supply to be used with a variety of different probes in different applications (e.g., dermatology, cardiac surgery, neurosurgery, arthroscopy, etc).

In some embodiments, probe 20 further includes an identification element that is characteristic of the particular electrode assembly so that the same power supply 28 can be used for different electrosurgical operations. In one embodiment, for example, the probe 20 includes a voltage reduction element or a voltage reduction circuit for reducing the voltage applied between the electrode terminals and return electrode 112. The voltage reduction element serves to reduce the voltage applied by the power supply so that the voltage between the electrode terminals and return electrode 112 is low enough to avoid excessive power dissipation into the electrically conductive medium, and/or to avoid excessive ablation of the tissue at the target site. The voltage reduction element primarily allows the electrosurgical probe 20 to be compatible with a range of electrosurgical generators (e.g., various generators supplied by ArthroCare Corporation, Sunnyvale, Calif.) that are adapted to apply higher voltages for ablation of tissue. For example, for contraction of tissue, the voltage reduction element will serve to reduce a voltage of about 100 to 135 volts RMS to about 45 to 60 volts RMS, which is a suitable voltage for contraction of tissue without ablating the tissue. Of course, for some procedures, the probe will typically not require a voltage reduction element. Alternatively, the probe may include a voltage increasing element or circuit, if desired.

Figure 6:
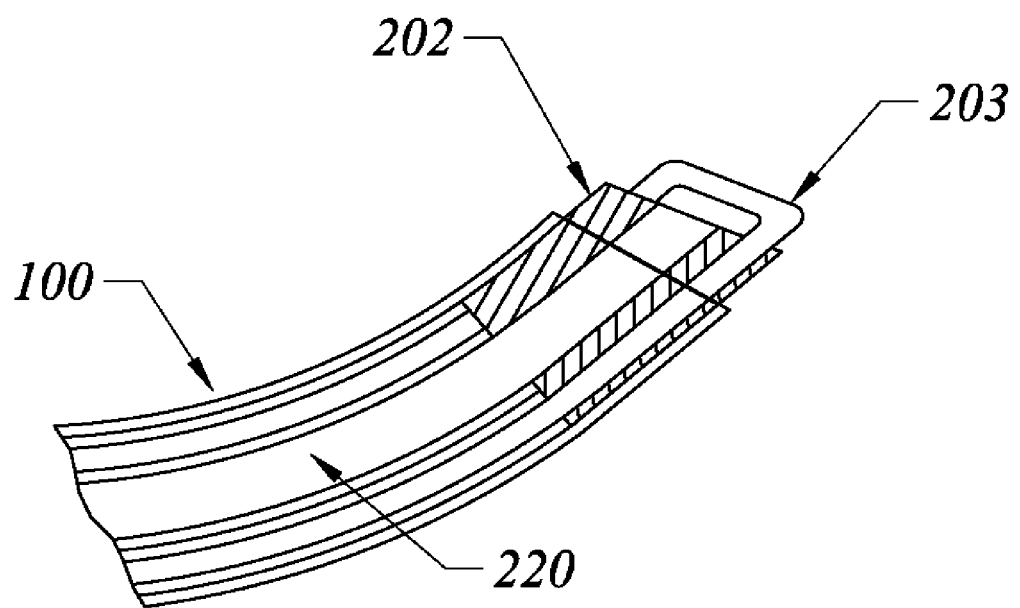

FIGS. 5-8 illustrate another embodiment of the present invention, incorporating an aspiration lumen and a loop electrode designed to ablate tissue fragments as they are aspirated into the aspiration lumen. As shown in FIG. 5, electrosurgical probe 20 includes an elongated shaft 100 which may be flexible or rigid, a handle 204 coupled to the proximal end of shaft 100, an electrode support member 102 coupled to the distal end of shaft 100, and a return electrode 112 disposed proximal to support member 102. As shown in FIG. 6, probe 20 includes an active loop electrode 203. Return electrode 112 (not shown in FIG. 6) is spaced proximally from active loop electrode 203. The probe 200 further includes a suction lumen 220 for aspirating excess fluids, bubbles, tissue fragments, and/or products of ablation from the target site. As shown in FIGS. 5 and 6, suction lumen 220 extends through support member 102, and terminates in a distal opening 222 (FIG. 8), and extends proximally to an external connector for coupling to a vacuum source (the latter well known in the art).

Figure 8:
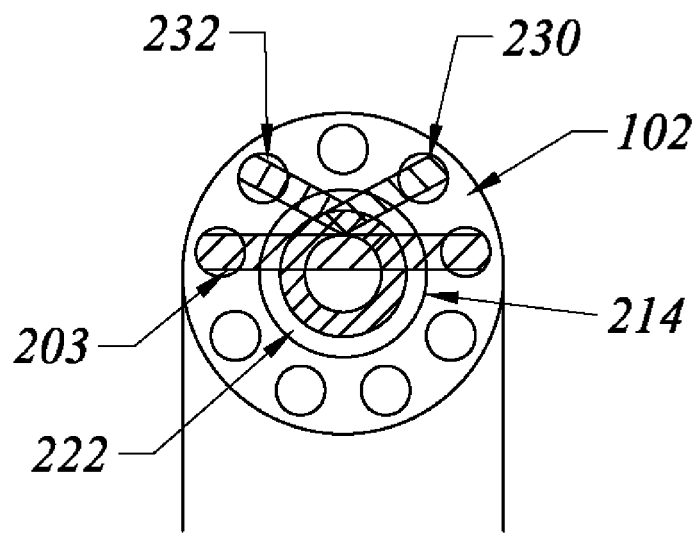

Again with reference to FIG. 5, electrode support member 102 extends from the distal end of shaft 100 and provides support for loop electrode 203 and a ring electrode 214 (FIG. 8). As shown in FIG. 8, loop electrode 203 has first and second ends extending from electrode support member 102. The first and second ends are each coupled to, or integral with, one or more connectors, e.g., wires, leads, or filaments (not shown), that extend through shaft 100 to the probe proximal end for coupling to the high frequency power supply. The loop electrode 203 usually extends about 0.5 to 10 mm from the distal end of support member 102, often about 1 to 2 mm Loop electrode 203 usually extends further away from support member 102 than ring electrode 214, in order to facilitate ablation of tissue. As discussed below, loop electrode 203 is especially configured for tissue ablation, while ring electrode 214 ablates tissue fragments that are aspirated towards distal opening 222.

Referring to FIG. 8, ring electrode 214 preferably comprises a tungsten or titanium wire having two ends 230, 232 coupled to electrical connectors (not shown) within support member 102. The wire is bent to form one-half of a figure eight, thereby forming a ring positioned over opening 222 of suction lumen 220. This ring inhibits passage of tissue fragments large enough to clog suction lumen 220. Moreover, voltage applied between ring electrode 214 and the return electrode provide sufficient energy to ablate these tissue fragments into smaller fragments that are then aspirated through lumen 220. Typically, ring electrode 214 and loop electrode 203 are electrically isolated from each other. However, these electrodes 214, 203 may be electrically coupled in some applications.

Figure 9:
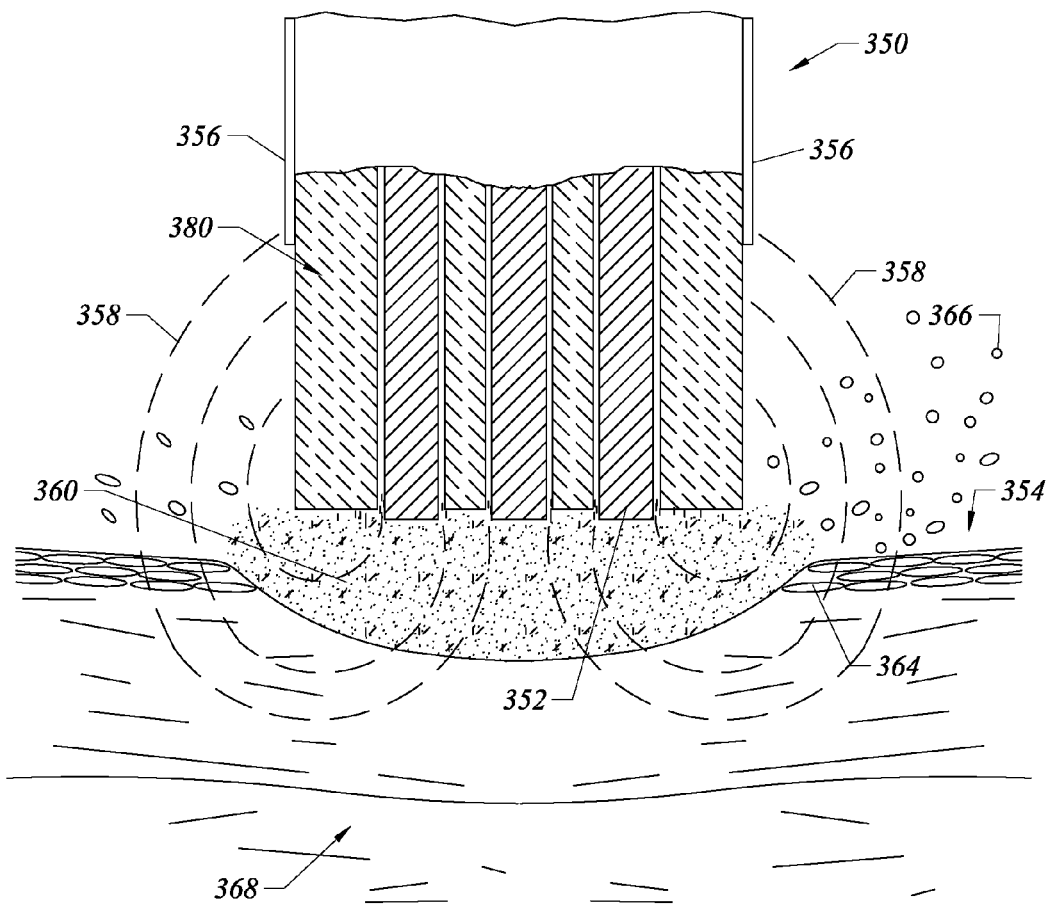
FIG. 9 illustrates a method of ablating tissue with a probe having a plurality of active electrodes according to the present invention.
Figure 10:
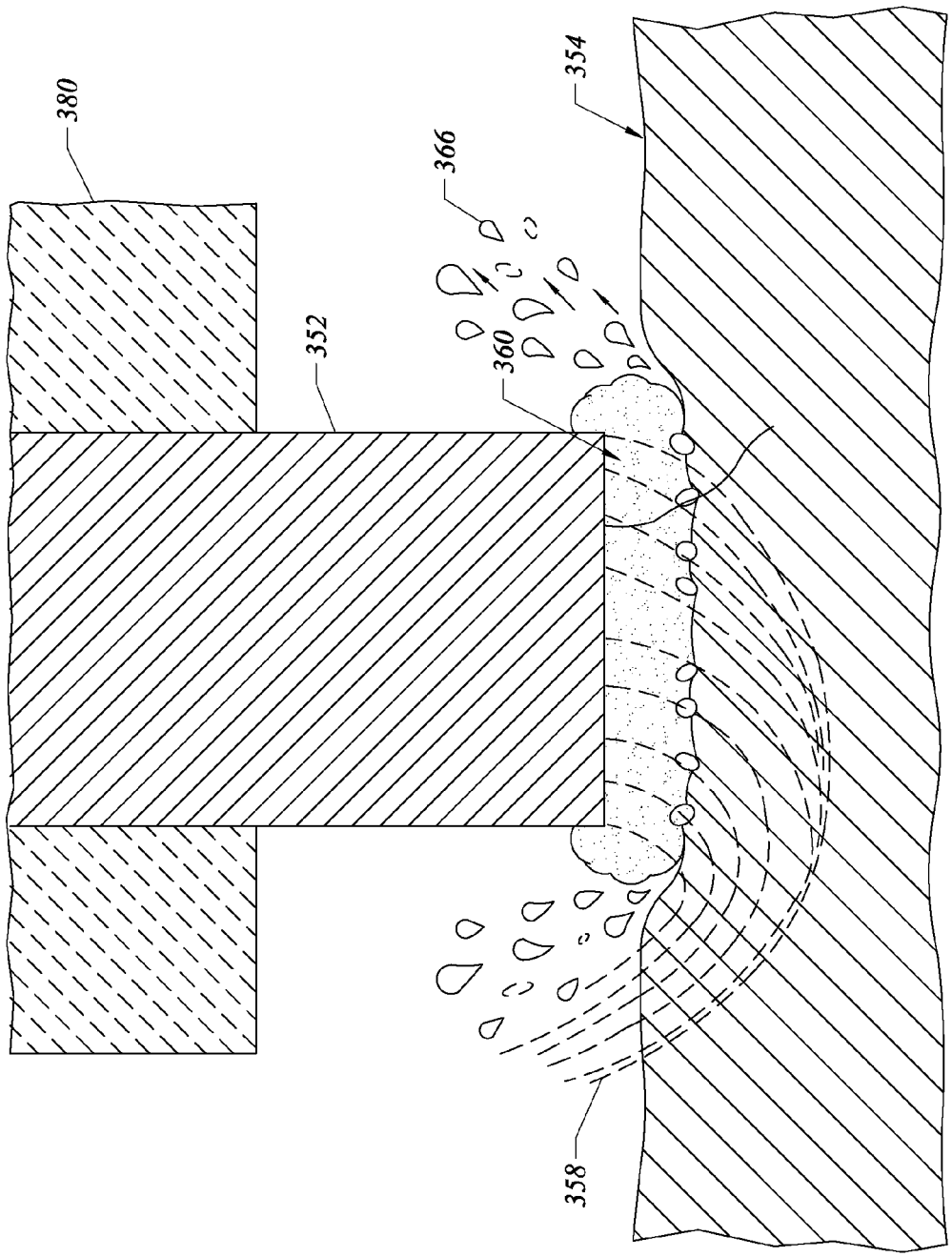
FIG. 10 illustrates a method of ablating tissue with a probe having a single active electrode according to the present invention.

FIGS. 9 and 10 illustrate use of a probe 350 of the present invention for ablating tissue. As shown, the distal portion of probe 350 is introduced to the target site (either endoscopically, through an open procedure, or directly on the patient's skin) and electrode(s) 352 are positioned adjacent to a target tissue. FIG. 9 illustrates a probe having multiple active electrodes 352, while FIG. 10 illustrates a probe having a single active electrode 352. In one embodiment, the target site is immersed in an electrically conductive fluid, such that the electrically conductive fluid generates a current flow path (see current flux lines 358) between a return electrode 356 and the active electrode(s) 352, and whereby the zone between the tissue 354 and electrode support 380 is constantly immersed in the electrically conductive fluid. The power supply (not shown) is then turned on and adjusted such that a high frequency voltage difference is applied between electrode terminal(s) 352 and return electrode 356

In the representative embodiment, the high frequency voltage is sufficient to convert the electrically conductive fluid between the target tissue 354 and active electrode terminal(s) 352 into an ionized vapor layer or plasma 360. As a result of the applied voltage difference between active electrode terminal(s) 352 and the target tissue 354 (i.e., the voltage gradient across the plasma layer 360, charged particles in the plasma (e.g., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue, and the production of low molecular weight gases 366, such as oxygen, nitrogen, carbon dioxide, hydrogen, and methane. This process can be precisely controlled, whereby damage to the underlying (non-target) tissue 368 is minimized or avoided.

Figure 11:
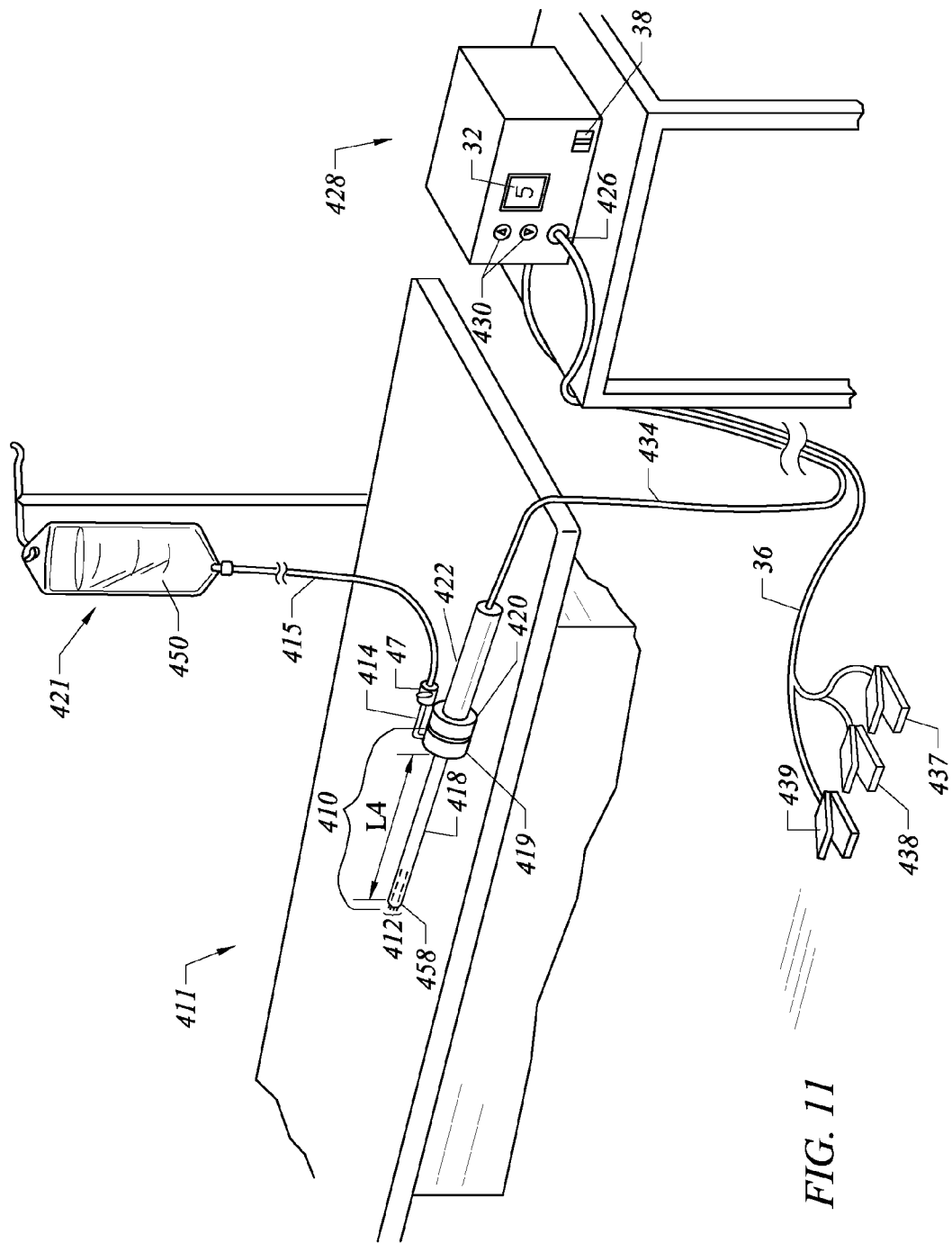
FIG. 11 is a perspective view of another electrosurgical system incorporating a power supply, an electrosurgical probe, and a source of electrically conductive fluid, according to another embodiment of the invention.

FIG. 11 schematically represents an electrosurgical system 411, according to another embodiment of the invention. System 411 is particularly useful in 'dry fields' where an electrically conductive fluid is preferably delivered via an electrosurgical probe 410 to the target site. Of course, system 411 may also be used in 'wet fields', i.e., the target site is immersed in an electrically conductive fluid. As shown, electrosurgical system 411 generally includes probe 410 connected to a power supply 428 for providing a high frequency voltage to probe 410, and a fluid source 421 for supplying electrically conductive fluid 450 to probe 410. In addition, electrosurgical system 411 may include an endoscope (not shown) with a fiber optic head light for viewing the surgical site. The endoscope may be integral with probe 410, or it may be part of a separate instrument. System 411 further includes first, second, and third foot pedals 437, 438, 439, for adjusting the voltage level of power supply 428, generally as described hereinabove. System 411 may also include an aspiration or suction element for aspirating excess fluid or unwanted materials from the surgical site.

As shown, probe 410 generally includes a proximal handle 419 and an elongate shaft 418 having an array 412 of electrode terminals 458 at its distal end. A connecting cable 434 has a connector 426 for electrically coupling the electrode terminals 458 to power supply 428. The electrode terminals 458 are electrically isolated from each other, and each of the terminals 458 is connected to an active or passive control network within power supply 428 by means of a plurality of individually insulated conductors (not shown). A fluid supply tube 415 is connected to probe 410 for supplying electrically conductive fluid 450 to the distal end of probe 410 or to the target site.

Figure 12:
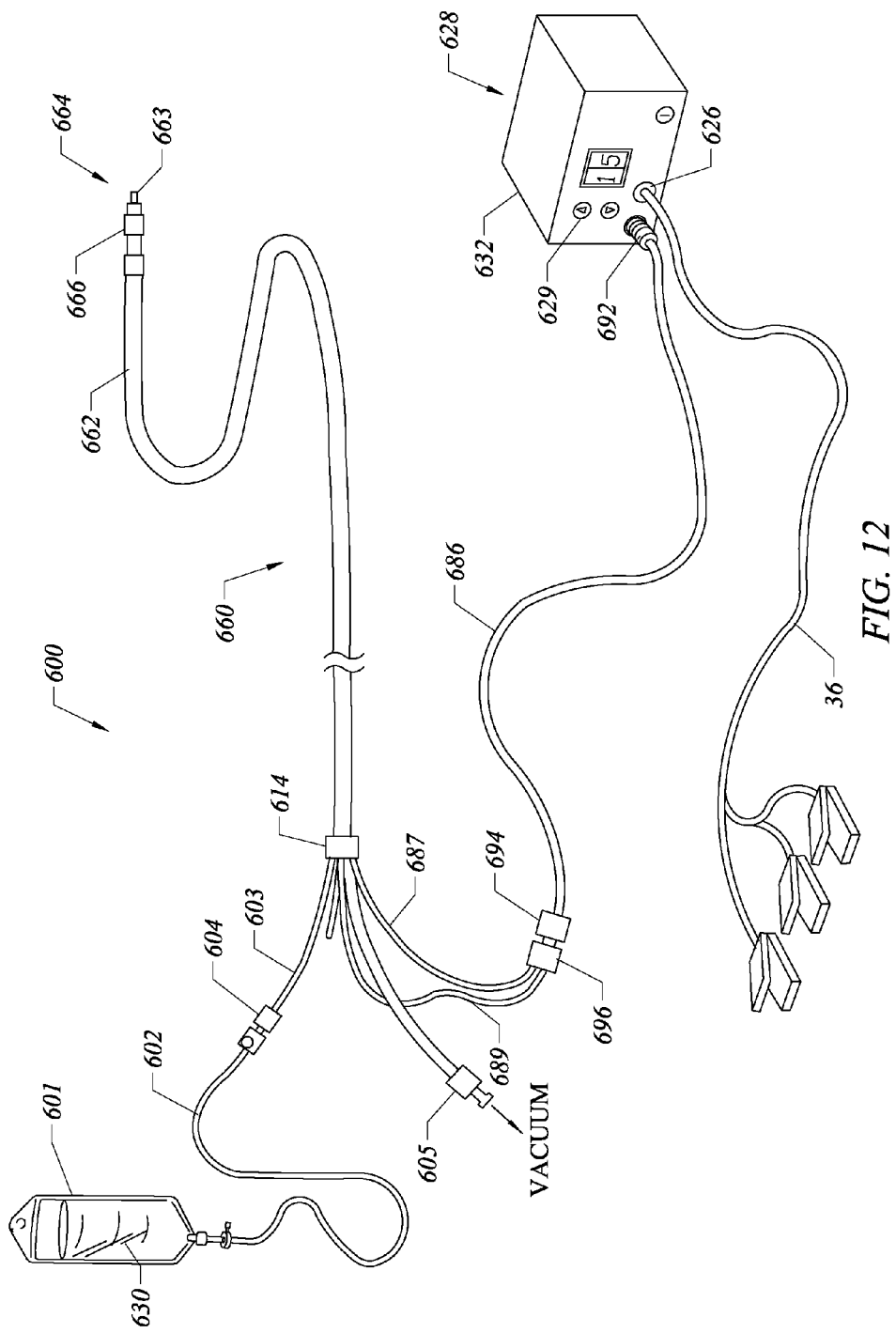
FIG. 12 is a perspective view of an electrosurgical catheter system, according to the present invention.

Referring to FIG. 12, an electrosurgical device according to the present invention may also be configured as an elongate catheter system 600, including portions with sufficient flexibility to permit introduction into the body and to the target site through one or more vascular lumen(s). As shown, system 600 generally comprises an electrosurgical catheter 660 connected to a power supply or generator 628 by an interconnecting cable 686 for providing high frequency voltage between active electrode(s) 663 and return electrode(s) 666, and an irrigant reservoir or fluid source 601 for providing electrically conductive fluid 630 to the target site. Catheter 660 generally comprises an elongate, flexible shaft body 662 including a tissue removing or ablating region 664 at the distal end of body 662. The proximal portion of catheter 660 includes a multi-lumen fitment 614 which provides for interconnections between lumens and electrical leads within catheter 660, and conduits and cables proximal to fitment 614. By way of example, a catheter electrical connector 696 is removably connected to a cable connector 694 which, in turn, is removably connectable to power supply 628 through connector 692. One or more electrically conducting lead wires (not shown) within catheter 660 extend between one or more active electrodes 663 at tissue ablating region 664 and one or more corresponding electrical terminals (also not shown) in catheter connector 696 via active electrode cable branch 687. Similarly, one or more return electrodes 666 at tissue ablating region 664 are coupled to a return electrode cable branch 689 of catheter connector 696 by lead wires (not shown). Of course, a single cable branch (not shown) may be used for both active and return electrodes.

Catheter body 662 may include reinforcing fibers or braids (not shown) in the walls of at least the distal ablating region 664 of body 662 to provide responsive torque control for rotation of ablating region 664 during tissue engagement. This rigid portion of the catheter body 662 typically extends only about 7 to 10 mm while the remainder of catheter body 662 is flexible to provide good trackability during advancement and positioning of active electrode(s) 663 adjacent target tissue.

Conductive fluid 630 is provided to tissue ablating region 664 of catheter 660 via a lumen (not shown in FIG. 12) within catheter 660. Fluid is supplied to the lumen from fluid source 601 along a conductive fluid supply line 602 and a conduit 603, which is coupled to the inner catheter lumen at multi-lumen fitment 614. A control valve 604 may be positioned at the interface of fluid supply line 602 and conduit 603 to allow manual control of the flow rate of electrically conductive fluid 630. Alternatively, a metering pump or flow regulator may be used to precisely control the flow rate of the conductive fluid. System 600 may further include an aspiration or vacuum system (not shown) to aspirate liquids and gases from the target site. The aspiration system will usually comprise a vacuum source coupled to fitment 614 by an aspiration connector 605.

Figure 13:
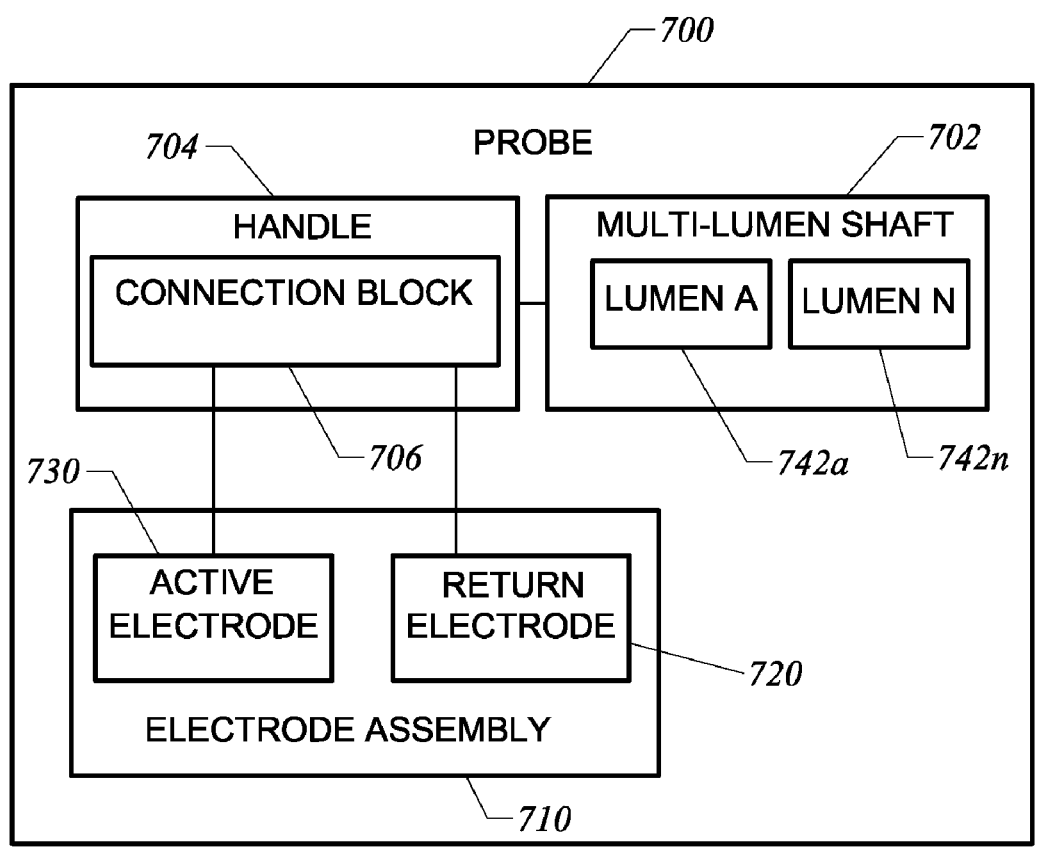
FIG. 13 is a block diagram schematically representing an electrosurgical probe, according to another embodiment of the invention.

FIG. 13 is a block diagram schematically representing an electrosurgical probe 700, according to another embodiment of the invention. Probe 700 includes a multi-lumen shaft 702, and a handle 704 housing a connection block 706. Connection block 706 is adapted for conveniently coupling probe 700 to a high frequency power supply (e.g., FIG. 1). Probe 700 further includes an electrode assembly 710, having a return electrode 720 and an active electrode 730. Return electrode 720 is coupled directly to connection block 706. Similarly, active electrode 730 is also coupled directly to connection block 706. Multi-lumen shaft 702 includes a plurality of lumens represented as lumen A 742a and lumen N 742n. Typically, multi-lumen shaft 702 is in the form of a cylinder over at least a portion of its length, and each of the plurality of lumens 742a, 742n are internal to the cylinder. In one embodiment, multi-lumen shaft 702 comprises a plastic tube formed by an extrusion process. Multi-lumen shaft 702 may include at least four internal lumens (e.g., FIG. 18A).

Figure 14:
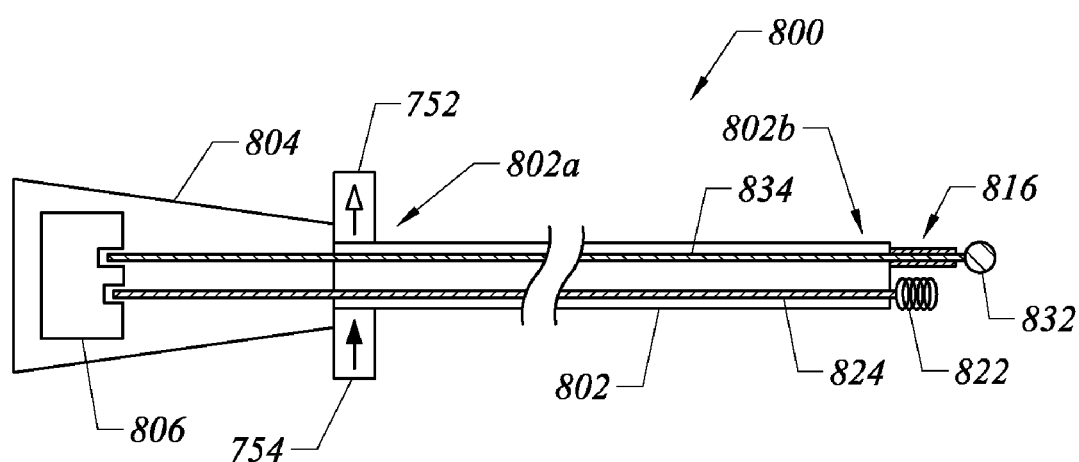
FIG. 14 is a partial longitudinal sectional view of an electrosurgical probe, according to one embodiment of the invention.

FIG. 14 is a partial longitudinal sectional view of an electrosurgical probe 800, according to one embodiment of the invention. Probe 800 includes a shaft 802 having a shaft proximal end portion 802a and a shaft distal end portion 802b. Probe 800 also includes a handle 804 housing a connection block 806. Probe 800 further includes a return electrode comprising a return electrode filament 824 and a return electrode head 822. As shown, return electrode head 822 is in the form of a coil having a plurality of turns. Typically, return electrode head 822 comprises a coil having up to about 50 turns, usually from about 3 to 10 turns, often from about 4 to 8 turns, and more typically about 6 turns (e.g., FIGS. 16A-16B). The proximal end of return electrode filament 824 is coupled directly to connection block 806. In one embodiment, the return electrode is formed by removing an insulating layer from a distal end portion of a length of wire, and winding the distal end of the wire into a coil to form return electrode head 822, wherein the proximal end of the wire is adapted for direct coupling to connection block 806. In this way, the return electrode conducts electric current from the distal tip of probe 800 to connection block 806 as a single component. Return electrode filament 824 and return electrode head 822 may be formed from a wire comprising a metal such as platinum, molybdenum, tungsten, titanium, nickel, iridium, or their alloys. Typically, return electrode filament 824 is encased within an electrically insulating layer over at least a portion of its length.

Probe 800 still further includes an active electrode comprising an active electrode filament 834 and an active electrode head 832. Active electrode head 832 may be in the form of a metal disc, or a flattened coil having from about 0.5 to 1.5 turns, and often about 1 turn (e.g., FIGS. 19A-D, 20A-B). Other geometries for the active electrode head are also contemplated and are within the scope of the invention (e.g., FIG. 21). The proximal end of active electrode filament 834 is coupled directly to connection block 806. Active electrode filament 834 and active electrode head 832 may be formed from a wire comprising a metal such as platinum, molybdenum, tungsten, titanium, nickel, iridium, or their alloys. An electrically insulating spacer 816 encircles the distal end of active electrode filament 834. As an example, spacer 816 may be a cylinder of a ceramic, a glass, or a silicone rubber. Spacer 816 prevents electrical shorting between active electrode head 832 and return electrode head 822, and also protects non-target tissue from exposure to the distal portion of active electrode filament 834 during a surgical procedure. According to one aspect of the invention, the active electrode filament and the electrically insulating spacer may lie within the coil of the return electrode head (e.g., FIGS. 16B-C).

In one embodiment, shaft 802 comprises a multi-lumen tube or shaft having at least a first lumen and a second lumen (e.g., FIG. 3), wherein return electrode filament 824 is accommodated in the first lumen, and active electrode filament 834 is accommodated in the second lumen. Probe 800 further includes a fluid delivery tube 754 for coupling to a source of electrically conductive fluid and for delivering an electrically conductive fluid (solid arrow) to return electrode head 822 and/or active electrode head 832 (e.g., FIGS. 17A-B, 18A-B). Probe 800 yet further includes an aspiration tube 752 for coupling to a vacuum source and for aspirating excess fluids and unwanted materials from a surgical site via an aspiration stream (open arrow). Fluid delivery tube 754 and aspiration tube 752 may be affixed to handle 804 or to shaft 802.

Figure 15:
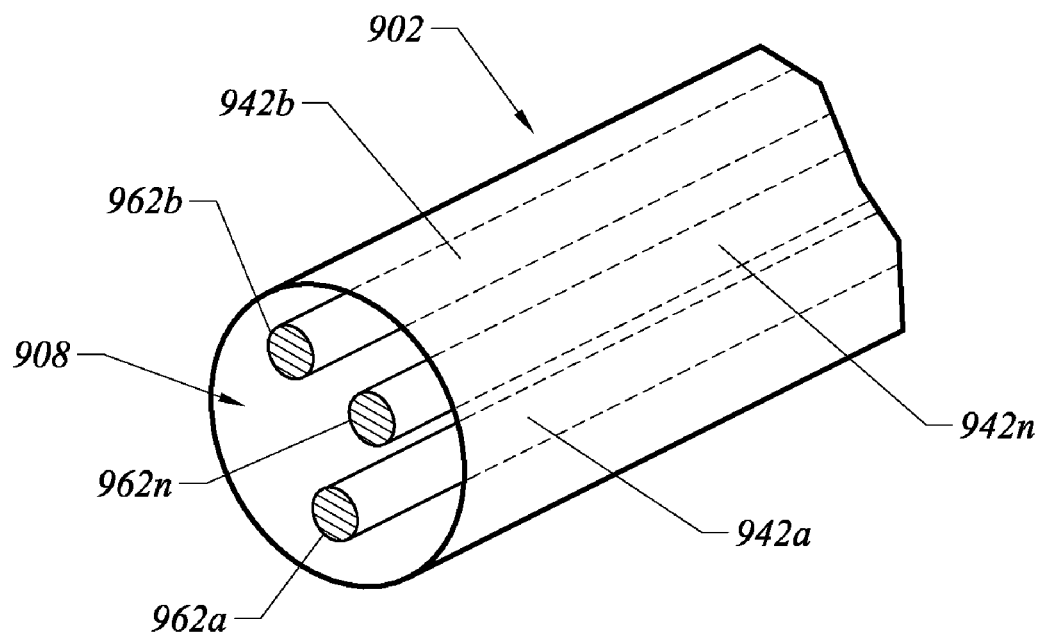
FIG. 15 is a perspective view of a multi-lumen probe shaft, according to the invention.

FIG. 15 is a perspective view of a multi-lumen shaft 902 of an electrosurgical probe, according to the invention. Multi-lumen shaft 902 includes a distal face 908 and a plurality of internal lumens represented as lumens 942a, 942b, 942n.

Each lumen terminates at distal face 908 in a corresponding port 962a, 962b, 962n. Multi-lumen shaft 902 may comprise a plastic tube, which may be formed, for example, by injection molding, blow molding, or extrusion. As an example, multi-lumen shaft 902 may comprise a polyether based thermoplastic polyurethane elastomer, such as Pellethane 2363 series (Dow Chemical). Multi-lumen shaft 902 may be pigmented or colorless. In one embodiment, multi-lumen shaft 902 is formed by extrusion of a polyurethane elastomer comprising from about 0.5% to 4% by weight of carbon black, more typically containing about 2% of carbon black.

Typically, multi-lumen shaft 902 is substantially cylindrical over at least part of its length. In one embodiment (not shown), multi-lumen shaft 902 is bent at an angle in the range of from about 20° C. to 30° C. A bend or curve in shaft 902 may facilitate access of the distal end of shaft 902 to a target tissue during a procedure. Internal lumens, e.g., 942a-n, may accommodate a lead or filament of a return electrode or of an active electrode (e.g., FIG. 16B). In addition, one or more of the internal lumens may serve as a conduit for an electrically conductive fluid, or for aspiration of excess materials from the surgical site (e.g., FIGS. 17A-B, 18A-B)

Figure 16A:
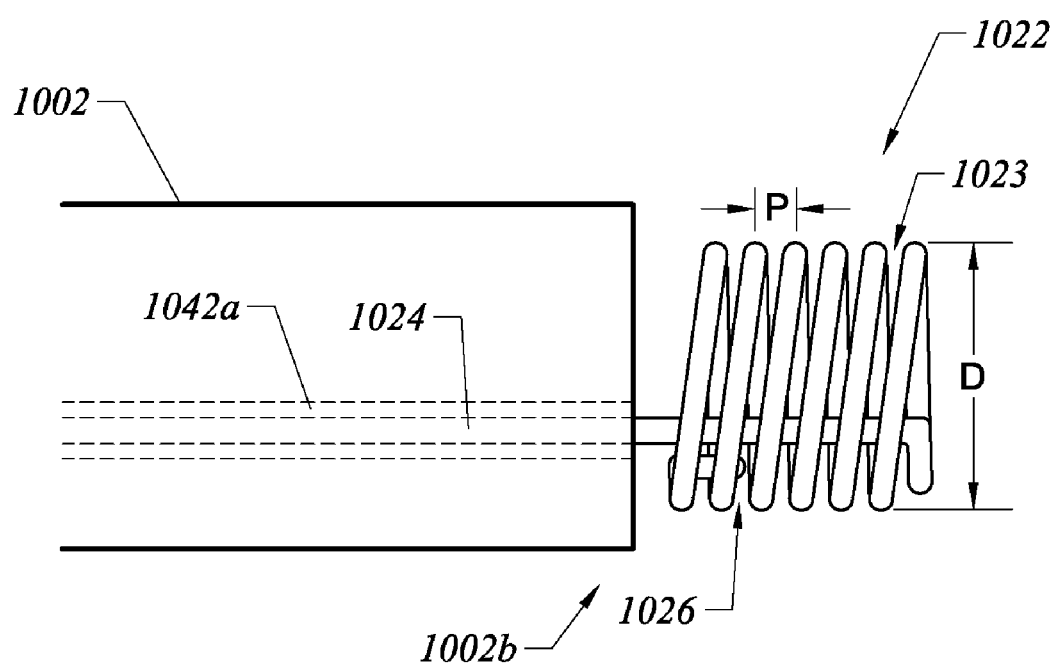
FIG. 16A is a side view of a return electrode in relation to the distal end of a probe shaft, according to one embodiment of the invention.

FIG. 16A is a side view of a return electrode, shown in relation to distal end 1002b of a shaft 1002 of an electrosurgical probe, according to one embodiment of the invention. The return electrode comprises a return electrode filament 1024, and a distal return electrode head 1022. Return electrode head 1022 is in the form of a coil. As shown, return electrode head 1022 comprises about 6 turns, however, other number of turns may also be used. Typically, return electrode head 1022 will comprise up to about 50 turns, and more typically from about 3 to 10 turns. Return electrode filament 1024 and return electrode head 1022 may be formed from a length of wire comprising a metal such as molybdenum, platinum, tungsten, palladium, iridium, titanium, or their alloys. As shown, return electrode head 1022 is wound in a proximal direction, wherein the first turn of the coil is at the distal end of the coil. After the last, i.e., most proximal, turn of the coil has been wound, a free end 1026 of the length of wire is arranged within an internal void defined by return electrode head 1022. As shown, the coil (or return electrode head 1022) and the internal void are substantially cylindrical. However, the coil of return electrode head 1022 and hence the internal void may have other shapes, e.g., frusto-conical shapes defined by tapering or expansion of the coil. For example, the coil may either taper or expand as it is wound in the proximal direction.

Again with reference to FIG. 16A, the coil of return electrode head 1022 has a pitch, P, which is usually in the range of from about from about 0.010 to 0.045 inch, and more typically from about 0.012 to 0.025 inch. As shown, a gap 1023 exists between each turn of return electrode head 1022. Gap 1023 allows an electrically conductive liquid, e.g., isotonic saline, to flow between the turns of return electrode head 1022, whereby both interior and exterior portions of return electrode head 1022 may be wetted by the electrically conductive liquid. Gap 1023 also promotes retention of electrically conductive liquid, e.g., via surface tension. Typically, return electrode head 1022 has an external diameter, D in the range of from about 0.050 to 0.200 inch, and more usually from about 0.070 to 0.150 inch. Return electrode filament 1024 is accommodated within a return electrode lumen 1042a within shaft 1002. Typically, return electrode filament 1024 is ensheathed within an electrically insulating coating (not shown), e.g., a layer of a polyimide.

Figure 16B:
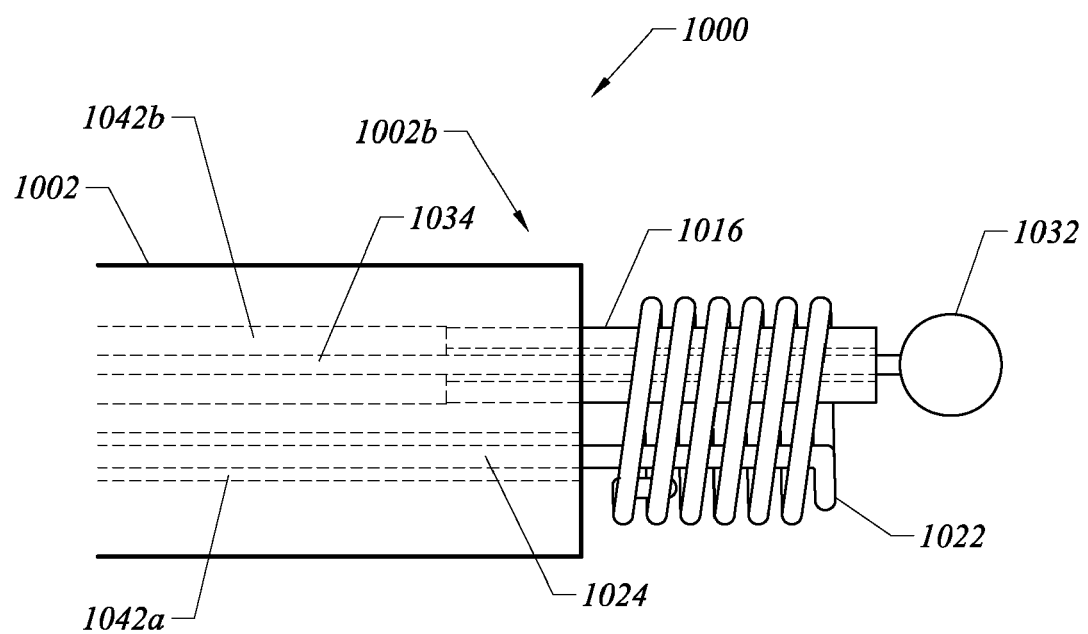
FIG. 16B is a side view of the distal portion of an electrosurgical probe including an active electrode and the return electrode of FIG. 16A, according to one embodiment of the invention.

FIG. 16B is a side view of the distal portion of an electrosurgical probe 1000, incorporating the return electrode of FIG. 16A. Probe 1000 includes an active electrode filament 1034 and an active electrode head 1032. Active electrode filament 1034 is accommodated within an active electrode lumen 1042b. The distal portion of active electrode filament 1034 is encircled within an electrically insulating spacer 1016. The proximal portion of spacer 1016 is inserted within shaft distal end portion 1002b. Spacer 1016 and the distal portion of active electrode filament 1034 lie within return electrode head 1022. Active electrode head 1032 may be in the form of a metal disc, or a flattened coil (e.g., FIGS. 19A-D). In the latter embodiment, the active electrode coil is arranged substantially orthogonal to the coil of return electrode head 1022. Typically, the surface area of the return electrode coil is at least about twice (two times) the surface area of the active electrode head, and more typically, from about two times to about 20 times the surface area of the active electrode head. The relatively large surface area of the return electrode coil prevents inadvertent firing of the return electrode during use of probe 1000.

Figure 16C:
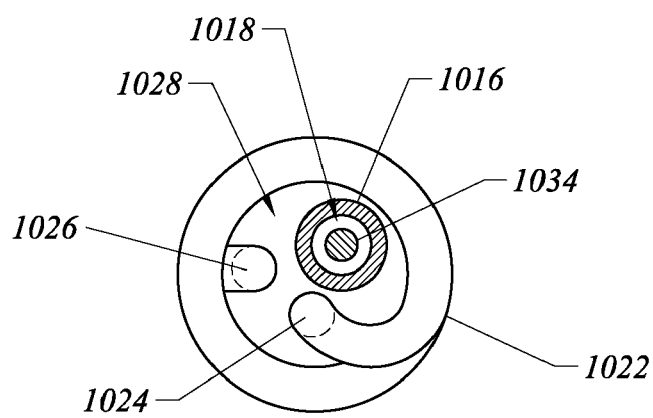
FIG. 16C is an end view of the return electrode of FIG. 16B showing an electrically insulating spacer encircling an active electrode filament within the return electrode, according to one embodiment of the invention.

FIG. 16C is an end view of return electrode head 1022 of FIG. 16B, indicating the positions of return electrode filament 1024 and free end 1026 within return electrode head 1022 at approximately six o'clock and nine o'clock, respectively. Thus, free end 1026 lies within an internal void 1028 of return electrode head 1022. However, other arrangements for return electrode filament 1024 and free end 1026 in relation to return electrode head 1022 are also possible under the invention. Spacer 1016 also lies within internal void 1028, and may comprise a cylinder of a glass, or a ceramic, e.g., alumina. Active electrode filament 1034 lies within spacer 1016. As shown, a substantially cylindrical void 1018 exists between active electrode filament 1034 and the inner wall of spacer 1016. Active electrode head 1032 is omitted from FIG. 16C for the sake of clarity.

Figure 17A:
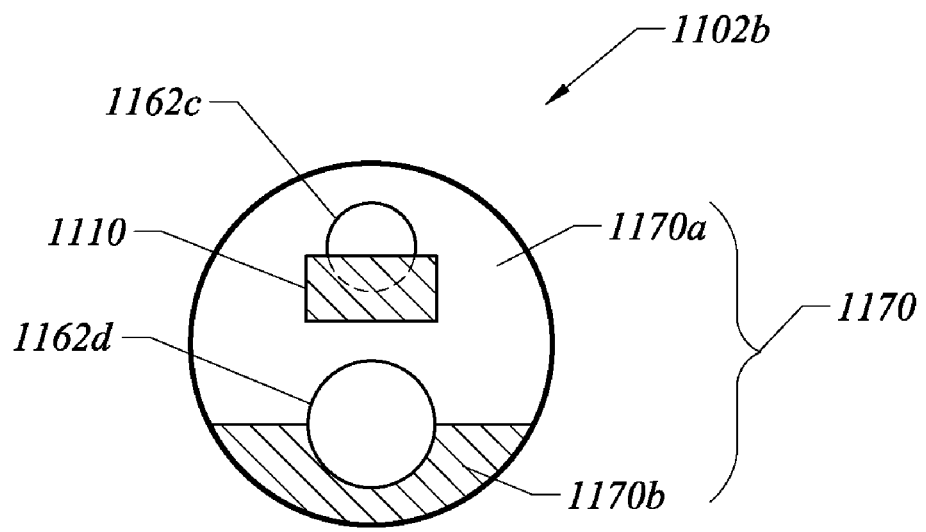
FIG. 17A is a face view of a shaft distal end having an aspiration port occupying a portion of two different planes.
Figure 17B:
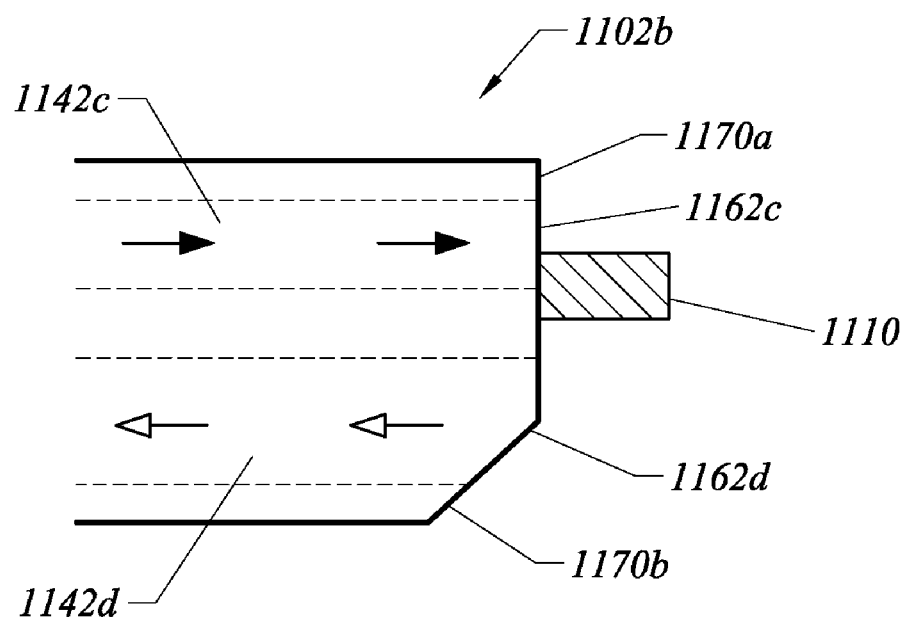
FIG. 17B is a side view of the shaft of FIG. 17A.

FIG. 17A is a face view, and FIG. 17B is a side view, of a shaft distal end 1102b of an electrosurgical probe, according to another embodiment of the invention. A distal face 1170 of shaft distal end 1102b includes a first plane 1170a and a second plane 1170b. A fluid delivery port 1162c is situated on first plane 1170a. An aspiration port 1162d occupies a portion of both first plane 1170a and second plane 1170b. Typically, in the embodiment shown in FIGS. 17A-B, second plane 1170b is beveled at an angle of from about 35° to 55°, and more typically at an angle of about 45°, with respect to first plane 1170a.

As shown in FIG. 17B, fluid delivery port 1162c and aspiration port 1162d are in communication with a fluid delivery lumen 1142c, and an aspiration lumen 1142d, respectively. Typically, fluid delivery lumen 1142c is coupled to a proximal fluid delivery tube (e.g., FIG. 14). Fluid delivery port 1162c is adapted for delivering an electrically conductive fluid to an electrode assembly 1110. Electrode assembly 1110 is disposed on shaft distal end 1102b. At least a portion of electrode assembly 1110 is aligned with fluid delivery port 1162c, such that an electrically conductive fluid (represented in FIG. 17B by solid arrows) emanating from fluid delivery port 1162c contacts electrode assembly 1110.

Aspiration port 1162d is adapted for aspirating excess electrically conductive fluid and unwanted materials, from shaft distal end 1102b, via an aspiration stream (open arrows) flowing proximally within aspiration lumen 1142d. Typically, aspiration lumen 1142d is coupled to an aspiration tube (e.g., FIG. 14), which in turn may be coupled to a suitable vacuum source. In one embodiment, aspiration lumen 1142d is coupled to a vacuum line or tube via a y-hub (not shown) connected to the proximal end portion of the probe shaft. Such a y-hub may comprise a plastic material, such as a polycarbonate, and the like. The force of the aspiration stream within aspiration lumen 1142*d* may be controlled or adjusted via a valve or analogous mechanism, as is well known in the art. By arranging aspiration port 1162*d* on both first plane 1170*a* and second plane 1170*b*, the surface area of aspiration port 1162*d* is increased for an aspiration lumen of a given diameter. Applicants have observed that, by arranging aspiration port 1162*d* on two different planes, aspiration port 1162*d* is less likely to become clogged (e.g., by resected tissue fragments, or other particulate matter aspirated from the milieu of the target tissue).

Figure 18A:
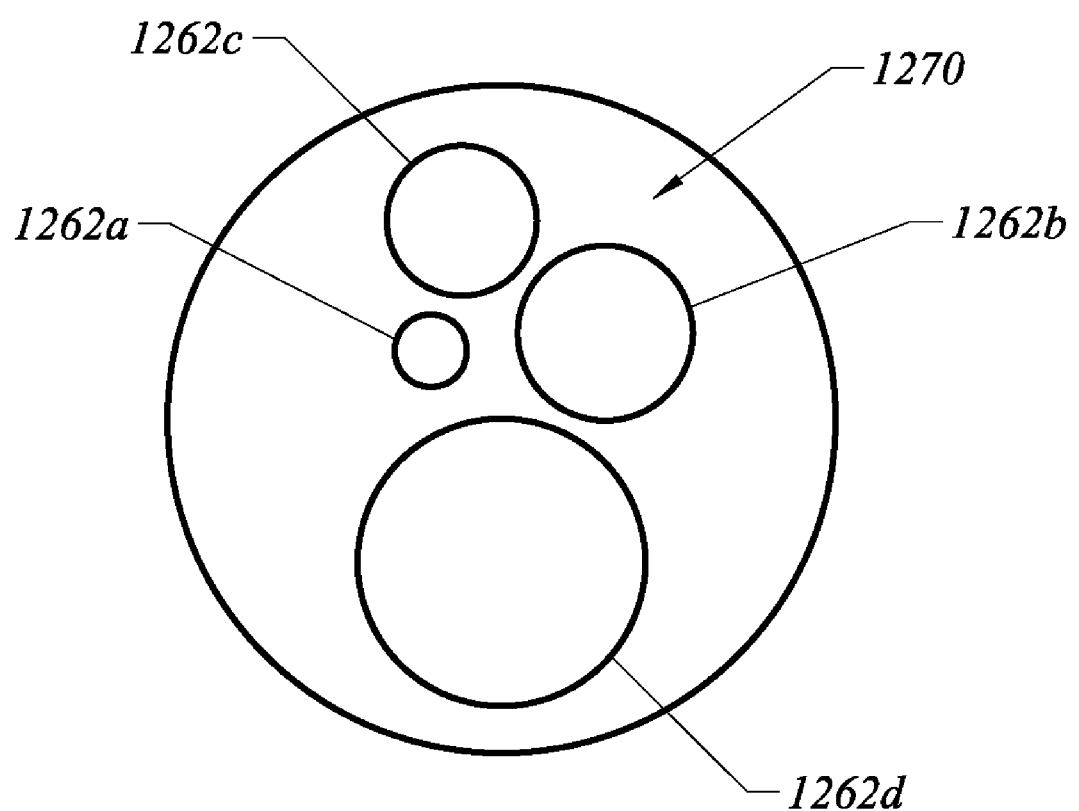
FIG. 18A is an end view of a multi-lumen shaft showing a plurality of ports on the distal face of the shaft.

FIG. 18A is an end view of a multi-lumen shaft of an electrosurgical probe, showing a specific configuration of a plurality of ports on shaft distal face 1270, according to one embodiment of the invention. Thus, there is shown first, second, third, and fourth ports 1262*a*, 1262*b*, 1262*c*, 1262*d*, respectively. Each of first, second, third, and fourth ports 1262*a*, 1262*b*, 1262*c*, 1262*d* is in communication with a corresponding lumen within the shaft of the probe (e.g., analogous to lumens 942*a-n* of FIG. 15). A return electrode and an active electrode (e.g., FIG. 18B) are omitted from FIG. 18A for the sake of clarity.

Figure 18B:
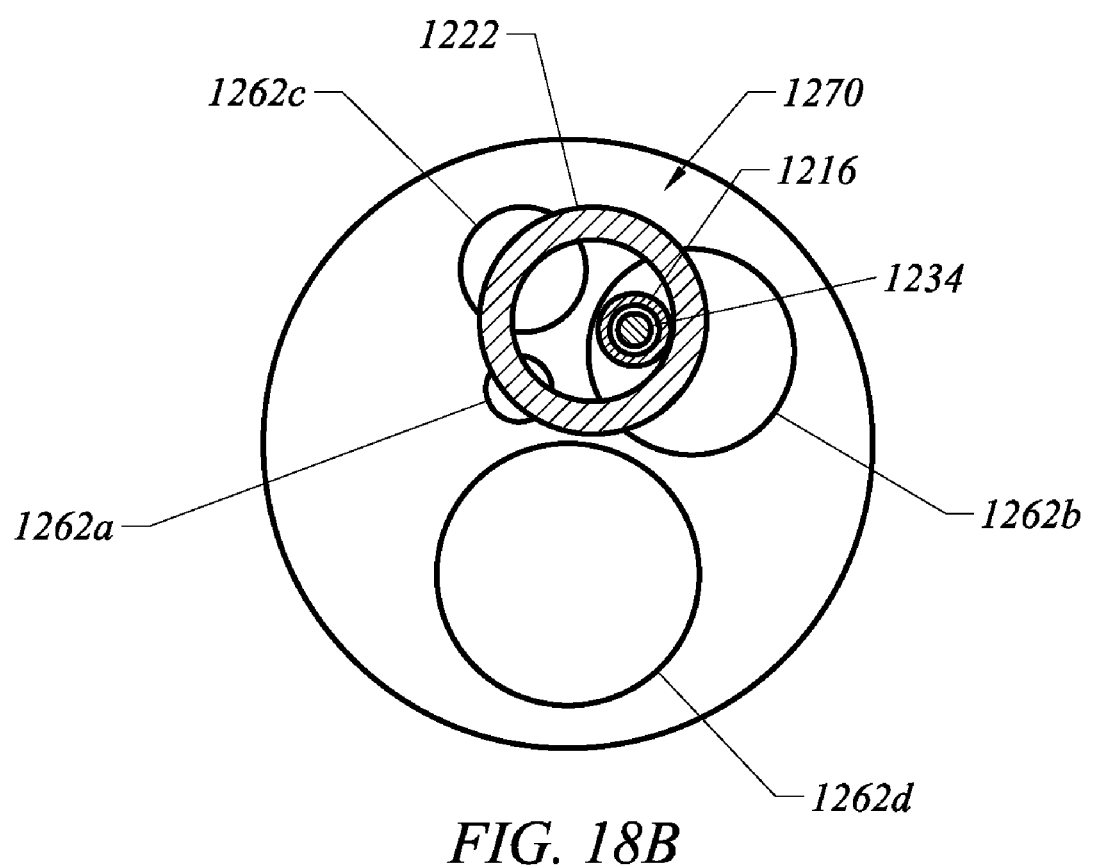
FIG. 18B shows the location of a return electrode head and an active electrode filament in relation to the shaft distal face of FIG. 18A, according to one embodiment of the invention.

With reference to FIG. 18B, the location of a return electrode head 1222 is shown with respect to first, second, third, and fourth ports 1262*a*, 1262*b*, 1262*c*, 1262*d*. A return electrode filament (not shown) emanates from first port 1262*a* and leads distally to return electrode head 1222. Typically, return electrode head 1222 is in the form of a coil having from about 3 to 10 turns (e.g., FIGS. 16A-B). Third port 1262*c* comprises a fluid delivery port from which an electrically conductive fluid is delivered during use of the probe. A portion of return electrode head 1222 is aligned with third port 1262*c*, such that electrically conductive fluid delivered from third port 1262*c* contacts both external and internal portions of the coil of return electrode head 1222.

An active electrode filament 1234 emanates from second port 1262*b*, and together with an electrically insulating spacer 1216, lies within return electrode head 1222. Active electrode filament 1234 leads distally to an active electrode head (omitted from FIG. 18B for the sake of clarity). Typically, the active electrode head is in the form of a flattened coil, having at least one void therein (e.g., FIGS. 19A-D, 20A-B). Fourth port 1262*d* comprises an aspiration port for aspirating unwanted materials from a surgical site during a procedure.

FIGS. 19A-D illustrate an active electrode 1330 for an electrosurgical probe, according to one embodiment of the invention. FIG. 19A is a side view of active electrode 1330. Active electrode 1330 includes an active electrode filament 1334 and an active electrode head 1332 at the distal end of filament 1334. Active electrode head 1332 is in the form of a coil defining an internal void 1337. At least one edge of the active electrode coil (e.g., edge 1338, FIG. 19D) is offset from the longitudinal axis of filament 1334 by a minimum distance in the range of from about 0.008 to about 0.016 inches. Active electrode head 1332 includes a dividing portion 1336. Typically, dividing portion 1336 is arranged at an angle in the range of from about 30° to 60° to the longitudinal axis of filament 1334. As shown, the coil of active electrode 1332 comprises about 1 turn, and dividing portion 1336 spans the coil at an angle of about 45° to the longitudinal axis of filament 1334, such that internal void 1337 is divided into two substantially equal portions. Internal void 1337 promotes retention of an electrically conductive fluid delivered to active electrode head 1332. The presence of electrically conductive fluid in the vicinity of active electrode head 1332 facilitates initiation and maintenance of a plasma at active electrode head 1332 upon application of a suitable high frequency voltage between active electrode 1330 and a return electrode (e.g., return electrode 1022, FIG. 16B).

FIG. 19B is a sectional view of active electrode filament 1334 taken along the lines 19B-19B of FIG. 19A. The proximal end of filament 1334 may be coupled directly to a connection block (e.g., FIG. 14). As can be seen from FIGS. 19A-B, a proximal portion of filament 1334 is encased within an electrically insulating layer 1333. Insulating layer 1333 may be a plastic, such as a polyimide. A distal portion of insulating layer 1333 is removed prior to constructing active electrode 1330 (e.g., FIG. 22). FIG. 19C is a sectional view of active electrode 1330 taken along the lines 19C-19C of FIG. 19A within a flattened portion 1335 of electrode 1330.

FIG. 19D is an end view of active electrode head 1332 as seen along the lines 19D-19D of FIG. 19A, and indicates a pointed or sharp edge portion 1338. Typically, the coil of active electrode head 1332 has a diameter, D' in the range of from about 0.050 to 0.150 inch, and usually from about 0.075 to 0.120 inch. The coil of active electrode head 1332 usually has a width, W in the range of from about 0.003 to 0.012 inch, and more typically from about 0.005 to 0.010 inch. The edges of dividing portion 1336 may have the same or similar geometry as edge portion 1338. Applicant has observed that pointed or sharp edges on an external surface of an electrode terminal of an electrosurgical probe may promote facile cutting of tissue and rapid ablation of tissue. Active electrode 1330 is adapted for coagulation of tissue, and for effecting hemostasis, when a side 1332*a* or 1332*b* of active electrode head 1332 is engaged against the tissue. Active electrode 1330 is further adapted for severing, cutting, or excising tissue when active electrode head 1332 is translated in the plane of electrode head 1332 (in any direction (e.g., up, down, back, forth) with respect to the tissue). Active electrode 1330 is still further adapted for volumetric removal (ablation) of tissue when active electrode head 1332 is translated (with respect to the tissue) in a direction substantially orthogonal to the plane of electrode head 1332.

Figure 20A:
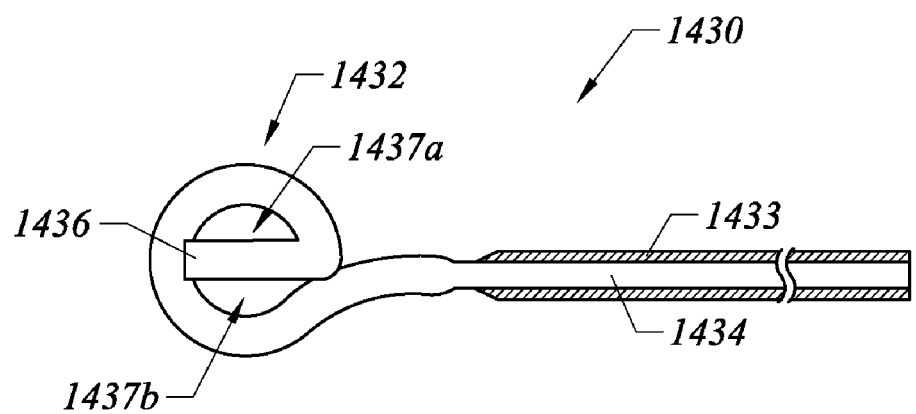
FIGS. 20A and 20B each show a side view of an active electrode having a flattened coil, according to two additional embodiments of the invention.

According to the invention, an active electrode head in the form of a coil may have less than 1 turn or more than one turn. Typically, such a coil comprises from about 0.5 to 1.5 turns. FIG. 20A shows a side view of an active electrode 1430, according to another embodiment of the invention. Active electrode 1430 includes an active electrode filament 1434 having an insulating layer 1433, and an active electrode head 1432 having a dividing portion 1436. Thus, active electrode 1430 has features similar or analogous to active electrode 1330 (FIG. 19A). Active electrode head 1432 comprises a flattened coil having somewhat less than one turn (cf. FIG. 19A). Dividing portion 1436 of active electrode head 1432 spans an internal void within active electrode head 1432, wherein dividing portion 1436 is substantially parallel to filament 1434, and forms first and second voids 1337*a*, 1337*b*, respectively.

Figure 20B:
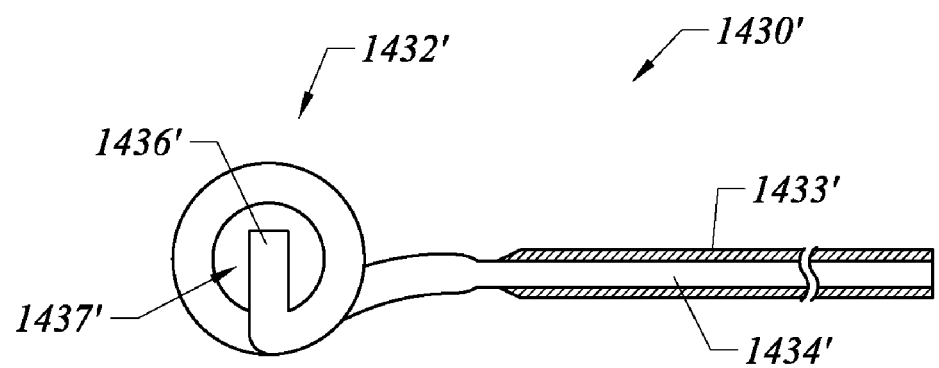
Figure 20C:
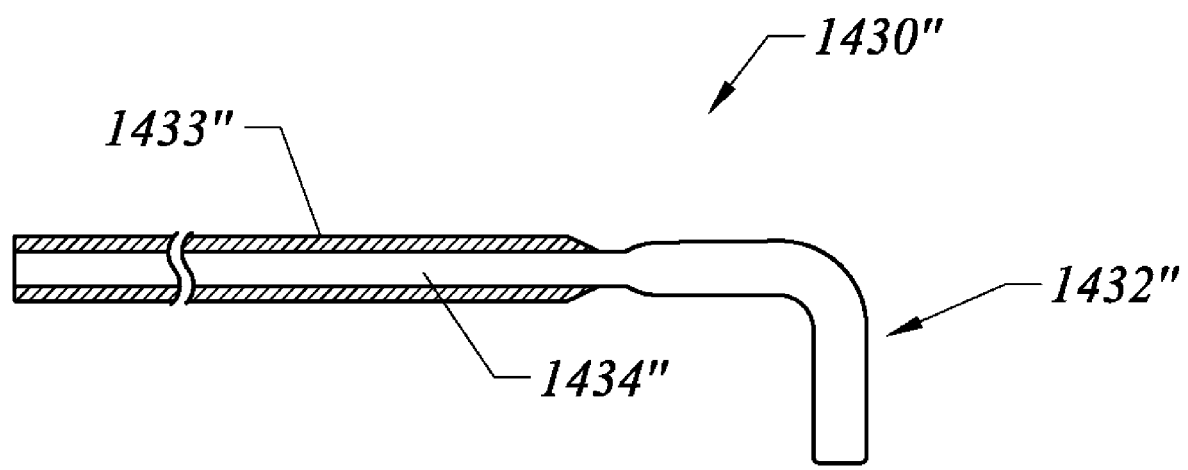
FIG. 20C is a side view of an active electrode having a hook, according to another embodiment of the invention.
Figure 21A:
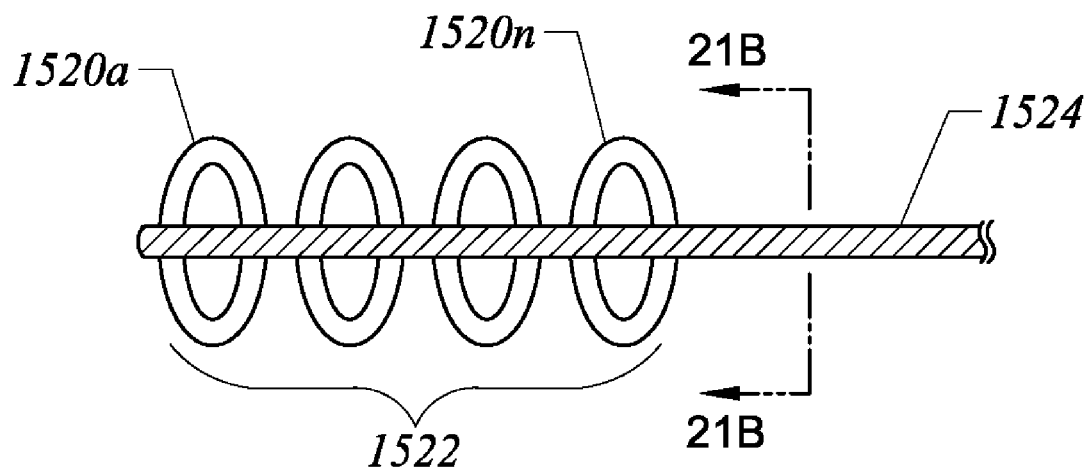
FIG. 21A is a perspective view of an active electrode terminal, according to another embodiment of the invention.
Figure 21B:
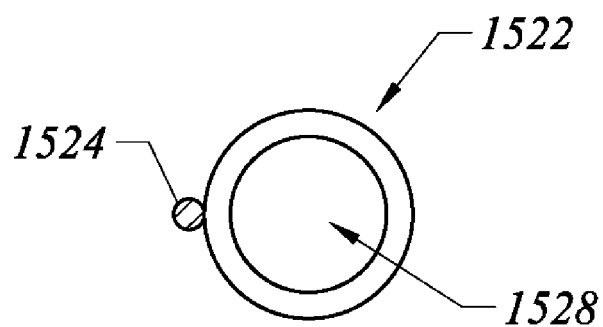
FIGS. 21B-D illustrates the active electrode terminal of FIG. 21A as taken along the lines 21B-21B, 21C-21C, and 21D-21D, respectively.
Figure 21C:
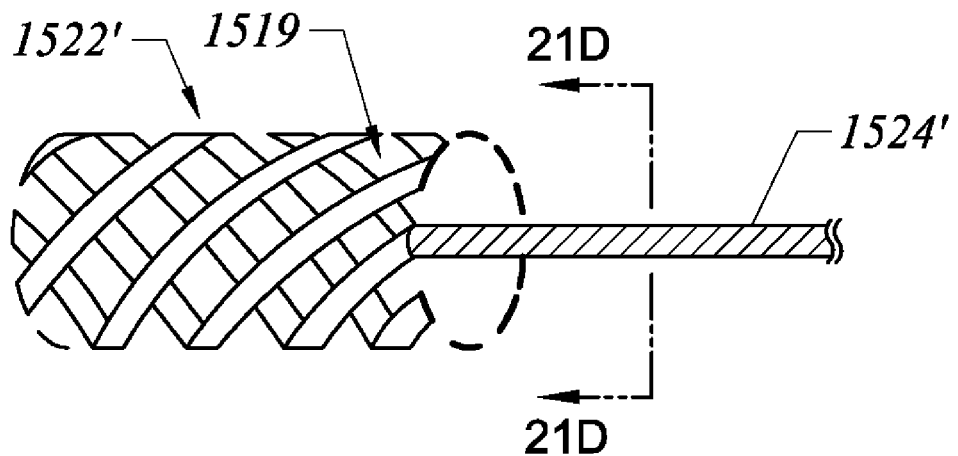
Figure 21D:
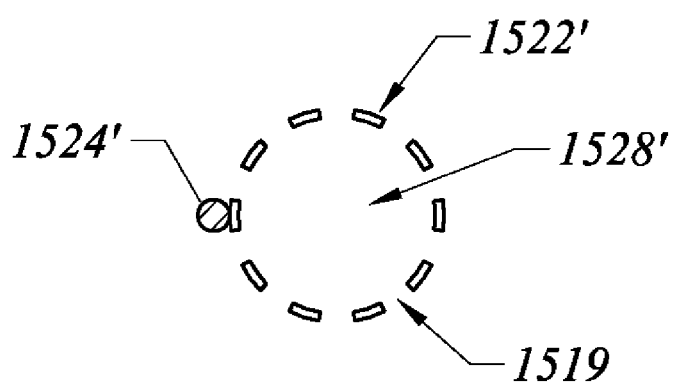

FIG. 20B shows a side of an active electrode 1430', according to another embodiment of the invention. Active electrode 1430' has certain features similar or analogous to those of active electrode 1430 (FIG. 20A). Thus, active electrode 1430' includes an active electrode filament 1434' having an insulating layer 1433', and an active electrode head 1432' having a dividing portion 1436'. Active electrode head 1432' comprises a flattened coil having somewhat more than one turn (cf. FIGS. 19A, 20A). In this embodiment, dividing portion 1436' terminates within an internal void 1437' of active electrode head 1432', and is arranged at an angle of about 90° with respect to the longitudinal axis of filament 1434'. Active electrodes having dividing portions arranged at other angles with respect to the active electrode filament are also within the scope of the invention.

FIG. 21 is a side view of an active electrode 1530, according to another embodiment of the invention. Active electrode 1530 includes an active electrode filament 1534 and an active electrode head 1432 at the distal end of filament 1534. Filament 1534 is ensheathed within an electrically insulating layer 1533. Insulating layer 1533 may comprise a plastic material, such as a polyimide. Active electrode head 1532 is in the form of a hook. Active electrode 1530 may be formed from a length of wire, wherein insulating layer 1533 is removed from the distal end thereof, and the distal end of the wire is bent and then flattened to form the hook portion. Active electrode head 1532 and filament 1534 may comprise a metal such as molybdenum, platinum, tungsten, palladium, iridium, titanium, or their alloys. Active electrode head 1532 is adapted for cutting or excising tissue when translated in the plane of electrode head 1532, and for volumetric removal of tissue when translated in a direction substantially orthogonal to the plane of electrode head 1532, essentially as described hereinabove for electrode 1330 (FIGS. 19A-D).

Figure 22:
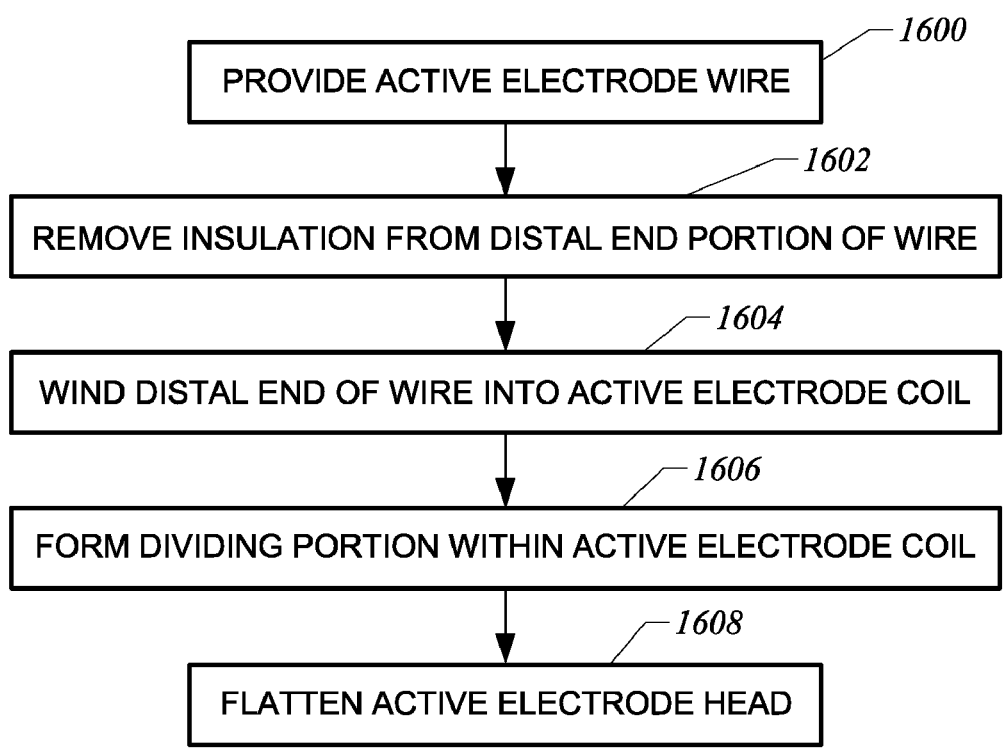
FIG. 22 schematically represents a number of steps involved in a method of making an active electrode, according to another embodiment of the invention.

FIG. 22 schematically represents a number of steps involved in a method of making an active electrode having an active electrode head in the form of a coil, according to the invention, wherein step 1600 involves providing a length of active electrode wire. Typically, the wire provided in step 1600 comprises a metal such as molybdenum, platinum, tungsten, palladium, iridium, titanium, or their alloys. The wire typically has a length in the range of from about 4 inches to 12 inches, usually from about 6 inch to 10 inch; and a diameter in the range of from about 0.006 inch to 0.020 inch, usually from about 0.010 inch to 0.016 inch. Typically, the length of wire provided in step 1600 is at least partially ensheathed within an electrically insulating layer, such as a polyimide coating.

Step 1602 involves removing the electrically insulating layer from the distal end of the length of wire. Step 1604 involves winding the distal end of the wire to form an active electrode head comprising a coil. The unwound portion of the length of wire proximal to the active electrode head comprises an active electrode filament. Typically, the active electrode head formed in step 1604 comprises a coil having from about 0.5 to 1.5 turns. In one embodiment, the distal end portion of the wire is bent at a location proximal to the active electrode head prior to winding the coil.

Step 1606 involves forming a dividing portion within the coil of the active electrode head. In one embodiment, the dividing portion spans the active electrode head and divides the internal void within the coil into two portions (e.g., FIGS. 19A, 20A). In another embodiment, the dividing portion terminates within the internal void of the coil (e.g., FIG. 20B). In one embodiment, the active electrode head, including the dividing portion, is formed by grasping the distal end of the length of wire with a pair of tweezers and wrapping the length of wire around the closed distal end of the tweezers. Step 1608 involves flattening the active electrode head. In one embodiment, step 1608 results in a substantially disc-like electrode head having sharp edges and one or more internal voids within the electrode head.

Figure 23:
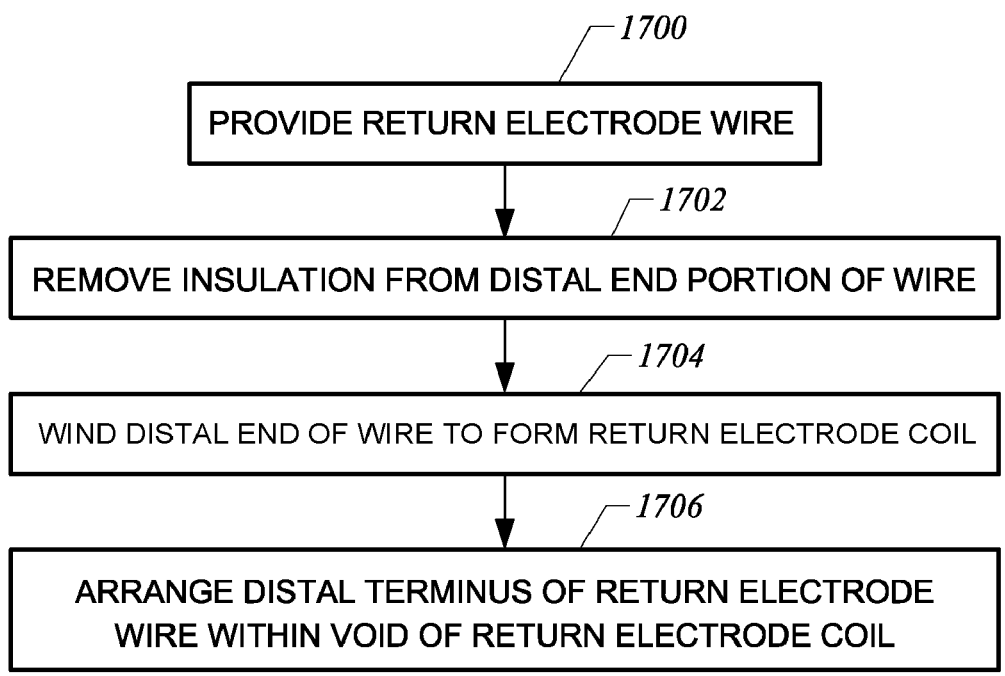
FIG. 23 schematically represents a number of steps involved in a method of making a return electrode, according to another embodiment of the invention.

FIG. 23 schematically represents a number of steps involved in a method of making a return electrode, according to the invention, wherein step 1700 involves providing a length of return electrode wire. Typically, the length of wire provided in step 1700 comprises a metal such as molybdenum, platinum, tungsten, palladium, iridium, titanium, or their alloys. The length of wire typically has a length in the range of from about 4 inches to 12 inches, usually from about 6 inch to 10 inch, and a diameter in the range of from about 0.008 inch to 0.030 inch, usually from about 0.012 inch to 0.020 inch. The length of wire provided in step 1700 is usually ensheathed within a layer of an electrically insulating material, such as a polyimide. Step 1702 involves removing the electrically insulating layer from the distal end portion of the length of wire.

Step 1704 involves winding the distal end portion of the wire to form a return electrode head comprising a coil. Typically, the return electrode head formed in step 1704 comprises a coil having from about 3 turn to 10 turns, and more usually about 6 turns. In one embodiment, step 1704 involves winding the coil in a proximal direction, wherein the first turn of the coil is located at the distal end of the return electrode head, and wherein the coil encircles the distal end of the return electrode filament (e.g., FIG. 16A). The return electrode head formed in step 1704 may be in the form of a cylindrical helix or a tapering (e.g., frusto-conical) helix. In one embodiment, after step 1704, step 1706 involves arranging the distal terminus of the return electrode wire within the internal void of the coil. Typically, the distal terminus of the return electrode wire is arranged against the interior of the coil at the proximal end of the return electrode head. The active electrode and the return electrode formed according to the methods of FIGS. 22 and 23 may be used in the construction of an electrosurgical probe of the invention (e.g., FIG. 24).

Figure 24:
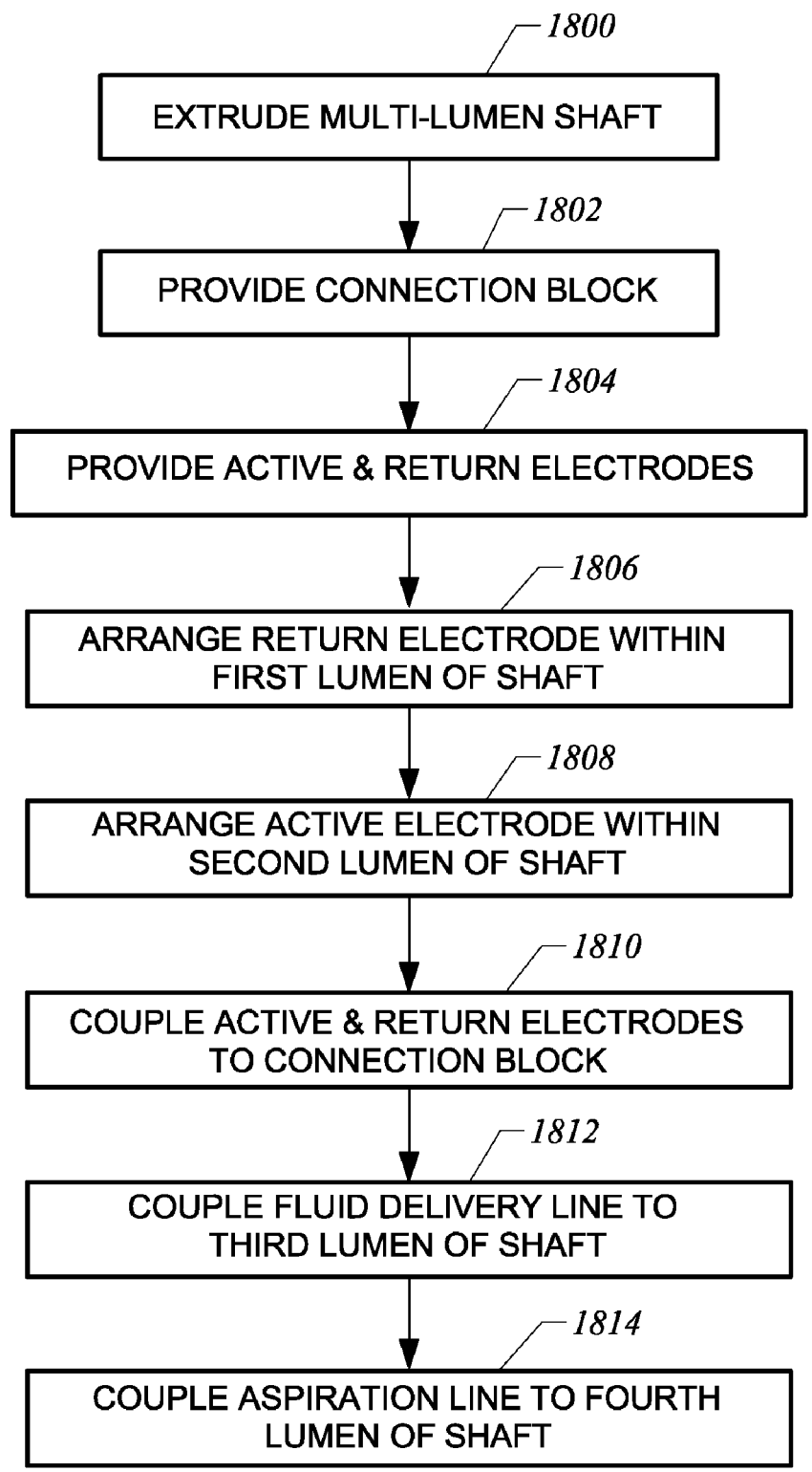
FIG. 24 schematically represents a number of steps involved in a method of making an electrosurgical probe, according to another embodiment of the invention.

FIG. 24 schematically represents a number of steps involved in a method of making an electrosurgical probe, according to another embodiment of the invention, wherein step 1800 involves forming a multi-lumen shaft or tube. In an exemplary embodiment, the multi-lumen shaft comprises a polyether based polyurethane elastomer formed by an extrusion process. However, other types of materials may also be used, and the shaft may also be formed by other processes, such as by injection molding or blow molding, the latter techniques well known in the art. The multi-lumen shaft includes a plurality of lumens, which may be of equal diameter or unequal diameter. Typically, the multi-lumen shaft is substantially cylindrical over at least a portion of its length, and at least two of the plurality of lumens are internal to the cylinder. In an exemplary embodiment, the multi-lumen shaft includes first, second, third and fourth internal lumens (e.g., FIG. 18A). In one embodiment, the multi-lumen shaft has a bend therein, at an angle in the range of from about 20° to 30°.

Step 1802 involves providing a connection block (e.g., connection block 806, FIG. 14). The connection block is adapted for the convenient, reliable, and facile coupling of the electrosurgical probe to a high frequency power supply or generator. Typically, the connection block is housed within a handle of the probe, and the handle is affixed to the proximal end of the multi-lumen shaft. Step 1804 involves providing an active electrode and a return electrode. In one embodiment, the active electrode comprises an active electrode filament bearing an active electrode head in the form of a metal disc or flattened coil having from about 0.5 to 1.5 turns (e.g., FIGS. 19A-D, 20A-B). The active electrode provided in step 1804 may be formed, for example, according to the method described hereinabove with reference to FIG. 22. In one embodiment, the return electrode comprises a return electrode filament bearing a return electrode head in the form of a helical coil having from about 3 to 10 turns (e.g., FIG. 16A). The return electrode provided in step 1804 may be formed, for example, according to the method described hereinabove with reference to FIG. 23.

Step 1806 involves arranging the return electrode within the first lumen of the multi-lumen shaft, such that the return electrode head protrudes from the distal end of the multi-lumen shaft, and such that the proximal end of the return electrode filament protrudes from the proximal end of the shaft and terminates in the region of the connection block.

Step 1808 involves arranging the active electrode within the second lumen of the multi-lumen shaft, such that the active electrode head protrudes from the distal end of the multi-lumen shaft, and such that the proximal end of the active electrode filament protrudes from the proximal end of the shaft and terminates in the region of the connection block. Typically, the active electrode is arranged within the second lumen of the multi-lumen shaft, such that the active electrode head protrudes axially from the distal end of the multi-lumen shaft. In one embodiment, the active electrode head is offset from the distal end of the multi-lumen shaft, wherein at least a portion of the active electrode head is out of axial alignment with the shaft distal end. This embodiment improves the surgeon's ability to view the active electrode head in relation to the target tissue during certain surgical procedures. In one embodiment, step 1808 involves arranging the active electrode within the coil of the return electrode head (e.g., FIGS. 16B-C). Step 1808 may further involve arranging the distal end of the active electrode filament within an electrically insulating spacer, wherein a proximal portion of the spacer is housed within the distal end of the second lumen, and wherein the distal end of the spacer protrudes axially from the distal end of the shaft.

Step 1810 involves coupling the proximal end of the return electrode filament to a first connector of the connection block, and independently coupling the proximal end of the active electrode filament to a second connector of the connection block. Step 1812 involves coupling a fluid delivery tube or line (e.g., FIG. 14) to the third lumen of the multi-lumen shaft, wherein the third lumen comprises a fluid delivery lumen for delivering an electrically conductive fluid to at least one of the return electrode head and the active electrode head. Step 1814 involves coupling an aspiration tube or line to the fourth lumen of the multi-lumen shaft, wherein the fourth lumen comprises an aspiration lumen for removing unwanted or excess material from the surgical site during a procedure.

Figure 25:
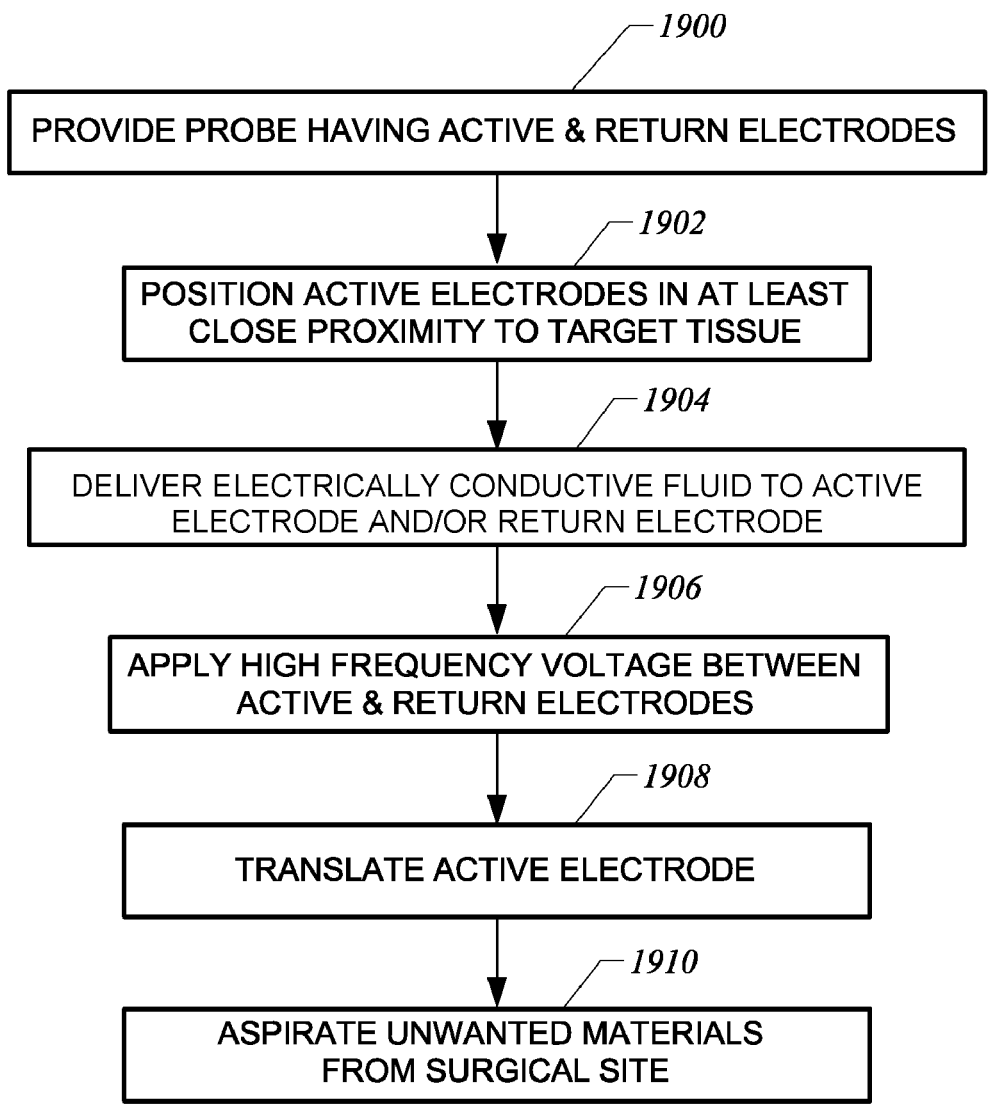
FIG. 25 schematically represents a number of steps involved in a method of treating a target tissue of a patient in vivo using an electrosurgical probe, according to another embodiment of the invention.

FIG. 25 schematically represents a number of steps involved in a method of treating a target tissue of a patient, in vivo, using an electrosurgical probe, according to another embodiment of the invention, wherein step 1900 involves providing an electrosurgical probe having an active electrode and a return electrode. The probe provided in step 1900 may have elements, features, or characteristics of the various electrosurgical probes described hereinabove (e.g., as described with reference to FIGS. 13-21). In one embodiment, the return electrode comprises a substantially cylindrical coil of wire having from about 3 to 10 turns. Typically, the probe further includes a connection block adapted for coupling the active and return electrodes to a high frequency power supply (e.g., FIG. 1). The high frequency power supply is typically adapted for operation in at least one of the ablation mode and the sub-ablation mode (as described hereinabove). In one embodiment, the probe provided in step 1900 features a multi-lumen shaft comprising a plastic material, wherein the multi-lumen shaft is formed by an extrusion process. The multi-lumen shaft may have a lumen for each of: fluid delivery to the distal or working end of the probe, aspiration of excess or unwanted materials from the surgical site, accommodating the active electrode filament or lead, and accommodating the return electrode filament or lead.

Step 1902 involves positioning the active electrode of the probe in at least close proximity to the target tissue. In one embodiment, the active electrode includes an active electrode head comprising a flattened coil having a dividing portion.

Step 1904 involves delivering an electrically conductive fluid, via a fluid delivery port and fluid delivery lumen, to the return electrode and/or to the active electrode. The electrically conductive fluid (e.g., isotonic saline) provides a current flow path between the active electrode and the return electrode. In one embodiment, the fluid delivery port is located on a distal face of the multi-lumen shaft, and at least a portion of the return electrode is aligned with the fluid delivery port. The return electrode may comprise a coil having a gap between at least two of the turns of the coil, wherein the gap promotes retention of the electrically conductive fluid thereat. In one embodiment, the active electrode head includes at least one void therein, and the at least one void in the active electrode head promotes the retention of the electrically conductive fluid in the region of the active electrode head.

Step 1906 involves applying, via the high frequency power supply, a high frequency voltage between the active electrode and the return electrode, wherein the high frequency voltage is sufficient to treat, modify, cut, or ablate the target tissue. The high frequency power supply may be operated in the ablation mode or the sub-ablation mode, as described hereinabove, according to the desired effect on the target tissue, e.g., in the ablation mode for the volumetric removal of tissue, and in the sub-ablation mode for shrinkage or coagulation of tissue. The actual voltage applied in step 1906 will generally be within the ranges cited hereinabove, for example, from about 70 volts RMS to 500 volts RMS in the ablation mode, and from about 10 volts RMS to 90 volts RMS in the sub-ablation mode.

Step 1908 involves translating the active electrode with respect to the target tissue. Typically, the probe includes a proximal handle, and the probe is translated in step 1908 by manipulating the probe via the handle. Step 1908 may involve translating the active electrode in the plane of the active electrode head, whereby the target tissue is severed, excised, transected, or cut. Alternatively or additionally, step 1908 may involve translating the active electrode in a direction substantially orthogonal to the plane of the active electrode head, whereby the target tissue is volumetrically removed or ablated. Typically, volumetric removal of target tissue according to the invention comprises plasma-induced molecular dissociation of target tissue components. Coagulation or hemostasis may be attained by engaging a side of the active electrode head against the target tissue, or against a severed vessel, while applying a suitable voltage to the probe (during step 1906, supra). Step 1910 involves aspirating any excess electrically conductive fluid, or other unwanted materials (such as resected tissue fragments) from the surgical site.

It will be apparent to the skilled artisan that the method described with reference to FIG. 25 is not restricted to a specific surgical procedure, nor to any particular type of procedure, but rather is applicable to a broad range of procedures in which controlled ablation, shrinkage, coagulation, or other electrosurgical modification of a target tissue is required.

While the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:
1. A method of treating a target tissue of a patient, comprising:
   a) providing an electrosurgical probe having an active electrode and a return electrode, the return electrode comprising a return electrode coil having an open tubular shape, the return electrode coil having from about 3 to 10 turns, a gap formed between the turns of the coil;

b) positioning the active electrode in at least close proximity to the target tissue and an electrically conductive fluid, the active electrode located at a distal end of an elongate member extending through said coil such that said active electrode is positioned distal to said coil, the gap adapted to allow the electrically conductive fluid to flow therethrough; and c) applying a high frequency voltage to the electrically conductive fluid between the active electrode and the return electrode sufficient to vaporize the electrically conductive fluid, wherein at least a portion of the tissue at the target site is ablated by the vaporized electrically conductive fluid.

2. The method of claim 1, wherein the active electrode comprises a flattened active electrode coil.

3. The method of claim 1, further comprising:
d) during said step c) translating the active electrode coil in the plane of the active electrode coil with respect to the target tissue, wherein the target tissue is severed.

4. The method of claim 1, further comprising:
e) during said step c), translating the active electrode coil in a direction orthogonal to the plane of the active electrode coil, wherein the target tissue is volumetrically removed.

5. The method of claim 1, further comprising:
f) during said step c), engaging at least one side of the active electrode coil against the target tissue, wherein the target tissue is coagulated.

6. The method of claim 1, wherein the active electrode comprises a hook, a coil, or a disc.

7. The method of claim 1, further comprising:
g) prior to said step c), delivering an electrically conductive fluid to the return electrode coil.

8. The method of claim 7, wherein the probe includes a shaft having a shaft distal end, the electrically conductive fluid delivered axially from the shaft distal end via a fluid delivery port.

9. The method of claim 8, wherein the electrically conductive fluid is delivered against interior and exterior surfaces of the return electrode coil.

10. The method of claim 1, further comprising:
h) aspirating unwanted materials from the surgical site via an aspiration lumen.

11. The method of claim 1, wherein the high frequency voltage applied in said step c) is in the range of from about 10 volts RMS to 500 volts RMS.

12. The method of claim 1, wherein during said step c) the target tissue is exposed to a temperature in the range of from about 40° C. to 90° C.

13. The method of claim 1, wherein the probe includes a shaft, the shaft comprising a multi-lumen tube having a plurality of lumens therein.

14. The method of claim 13, wherein the multi-lumen tube comprises a polyurethane elastomer extrusion.

15. A method of treating a target tissue of a patient, comprising:
positioning a distal section of an electrosurgical probe in close proximity to said tissue, said distal section comprising a return electrode coil having a plurality of turns and forming an open tubular shape, the coil having a plurality of turns, a gap formed between a plurality of the turns of the coil, said distal section further comprising an active electrode positioned on an elongate member extending through said coil and said active electrode being distal to said coil; and
applying a high frequency voltage to an electrically conductive fluid between the active electrode and the return electrode sufficient to vaporize the electrically conductive fluid such that at least a portion of the tissue at the target site is modified by the vaporized electrically conductive fluid.

16. The method of claim 15 wherein said return electrode comprises an exposed surface area greater than the surface area the active electrode.

* * * * *